US012741053B2

(12) United States Patent
Vatankhan-Varnosfaderani et al.

(10) Patent No.: US 12,741,053 B2
(45) Date of Patent: Sep. 22, 2026

(54) INJECTABLE AND MOLDABLE TISSUE-MIMETIC ELASTOMERS AND METHODS RELATED THERETO

(71) Applicant: UNIVERSITY OF NORTH CAROLINA AT CHAPEL HILL, Chapel Hill, NC (US)

(72) Inventors: Mohammad Vatankhan-Varnosfaderani, San Diego, CA (US); Sergei Sheiko, Chapel Hill, NC (US); Erfan Dashtimoghadam, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 1146 days.

(21) Appl. No.: 17/765,546

(22) PCT Filed: Oct. 2, 2020

(86) PCT No.: PCT/US2020/054022
§ 371 (c)(1),
(2) Date: Mar. 31, 2022

(87) PCT Pub. No.: WO2021/067765
PCT Pub. Date: Apr. 8, 2021

(65) Prior Publication Data

US 2022/0370679 A1 Nov. 24, 2022

Related U.S. Application Data

(60) Provisional application No. 62/910,089, filed on Oct. 3, 2019.

(51) Int. Cl.
*A61L 24/06* (2006.01)
*A61L 24/04* (2006.01)
(Continued)

(52) U.S. Cl.
CPC ............ *A61L 24/06* (2013.01); *A61L 24/046* (2013.01); *A61L 27/16* (2013.01); *A61L 27/18* (2013.01); *A61M 5/19* (2013.01); *A61L 2400/06* (2013.01)

(58) Field of Classification Search
None
See application file for complete search history.

(56) References Cited

U.S. PATENT DOCUMENTS 5,506,320 A 4/1996 Yu
2003/0185752 A1 10/2003 Nathan et al.
(Continued)

FOREIGN PATENT DOCUMENTS

WO WO-2007/140225 A2 12/2007
WO WO-2014/081819 A1 5/2014
(Continued)

OTHER PUBLICATIONS

Xu et al. (2016) "Fluorinated bottlebrush polymers based on poly(trifluoroethyl methacrylate): synthesis and characterization," *Polym. Chem.* 7: 680-688.
(Continued)

*Primary Examiner* — Dominic Lazaro
(74) *Attorney, Agent, or Firm* — Ballard Spahr LLP

(57) ABSTRACT

Materials and methods related to elastomers are disclosed. The disclosed elastomers are useful in implants mimicking soft tissue. This abstract is intended as a scanning tool for purposes of searching in the particular art and is not intended to be limiting of the present invention.

19 Claims, 31 Drawing Sheets

(51) Int. Cl.

| | |
|---|---|
| ***A61L 27/16*** | (2006.01) |
| ***A61L 27/18*** | (2006.01) |
| ***A61M 5/19*** | (2006.01) |

(56) References Cited

U.S. PATENT DOCUMENTS

| | | | |
|---|---|---|---|
| 2004/0110893 | A1 | 6/2004 | Matyjaszewski et al. |
| 2006/0018872 | A1 | 1/2006 | Tew et al. |
| 2010/0086897 | A1* | 4/2010 | Schulz-Walz ........ A61C 8/0069 433/201.1 |
| 2011/0093069 | A1* | 4/2011 | Goraltchouk ........... A61L 27/56 623/8 |
| 2011/0171712 | A1 | 7/2011 | Rivron et al. |
| 2013/0273115 | A1 | 10/2013 | Nguyen et al. |
| 2015/0125646 | A1 | 5/2015 | Tournilhac et al. |
| 2017/0183629 | A1 | 6/2017 | Alsberg et al. |
| 2018/0201785 | A1* | 7/2018 | Sheiko ...................... C08F 2/48 |
| 2020/0139005 | A1 | 5/2020 | Kaufmann et al. |

FOREIGN PATENT DOCUMENTS

| | | | |
|---|---|---|---|
| WO | WO-2017/015614 | A1 | 1/2017 |
| WO | WO-2019/046810 | A1 | 3/2019 |
| WO | WO-2019/046840 | A1 | 3/2019 |
| WO | WO-2019/152537 | A1 | 8/2019 |

OTHER PUBLICATIONS

Lendlein et al. (2005) "Shape-Memory Polymer Networks from Oligo(ϵ-caprolactone)Dimethacrylates," Journal of Polymer Science: Part A: Polymer Chemistry, 43: 1369-1381.

Nochel et al. (2013) "Shape-memory properties of hydrogels having a poly(ϵ-caprolactone) crosslinker and switching segment in an aqueous environment," European Polymer Journal, 49: 2457-2466.

Balani et al. 'Physical, Thermal, and Mechanical Properties of Polymers', Biosurfaces: A Materials Science and Engineering Perspective, (2014), Chapter AI, pp. 329-344.

Daniel et al. 'Bottlebrush-Guided Polymer Crystallization Resulting in Supersoft and Reversibly Moldable Physical Networks', Macromolecules, (2017), vol. 50, pp. 2103-2111 (Abstract).

Daniel et al. 'Solvent-free, supersoft and superelastic bottlebrush melts and networks', Nature Material, (2015), vol. 15, pp. 183-190.

Froes-Salgado et at Influence of the base and diluent monomer on network characteristics and mechanical properties of neat resin and composite materials, Odontology, (2014), vol. 103, pp. 160-168.

Shah et al. Tertiary Blends of PAMAM/PEG/PEL tissue bioadhesives, Journal of the Mechanical Behavior of Biomedical Materials, (2019), 101, 103405.

Sokolowski et al. 'Medical applications of shape memory polymers', Biomedical Materials, (2007), vol. 2, pp. S23-S27.

Vatankhah-Varnosfaderani et al. 'Chameleon-like elastomers with molecularly encoded strain-adaptive stiffening and coloration', Science, (2018), vol. 359, pp. 1509-1513.

Zhang et al. 'Anti-fouling Coatings of Poly(dimethylsiloxane) Devices for Biological and Biomedical Applications', Journal of Medical and Biological Engineering vol. 35, pp. 143-155(2015).

International Search Report and Written Opinion were mailed on Jan. 8, 2021 by the International Searching Authority for International Application No. PCT/US20/54022, filed on Oct. 2, 2020 and published as WO/2021/067765 on Apr. 8, 2021 (Applicant—The University of North Carolina at Chapel Hill) (9 pages).

International Search Report and Written Opinion were mailed on Jan. 31, 2019 by the International Searching Authority for International Application No. PCT/US2018/049300, filed on Sep. 3, 2018 and published as WO 2019/046810 on Mar. 7, 2019 (Applicant—The University of North Carolina at Chapel Hill) (10 Pages).

International Preliminary Report on Patentability was mailed on Mar. 3, 2020 by the International Searching Authority for International Application No. PCT/US2018/049300, filed on Sep. 3, 2018 and published as WO 2019/046810 on Mar. 7, 2019 (Applicant—The University of North Carolina at Chapel Hill) (9 Pages).

International Search Report and Written Opinion were mailed on Apr. 15, 2019 by the International Searching Authority for International Application No. PCT/US2019/015877, filed on Jan. 30, 2019 and published as WO 2019/152537 on Aug. 8, 2019 (Applicant—The University of North Carolina at Chapel Hill) (6 Pages).

* cited by examiner

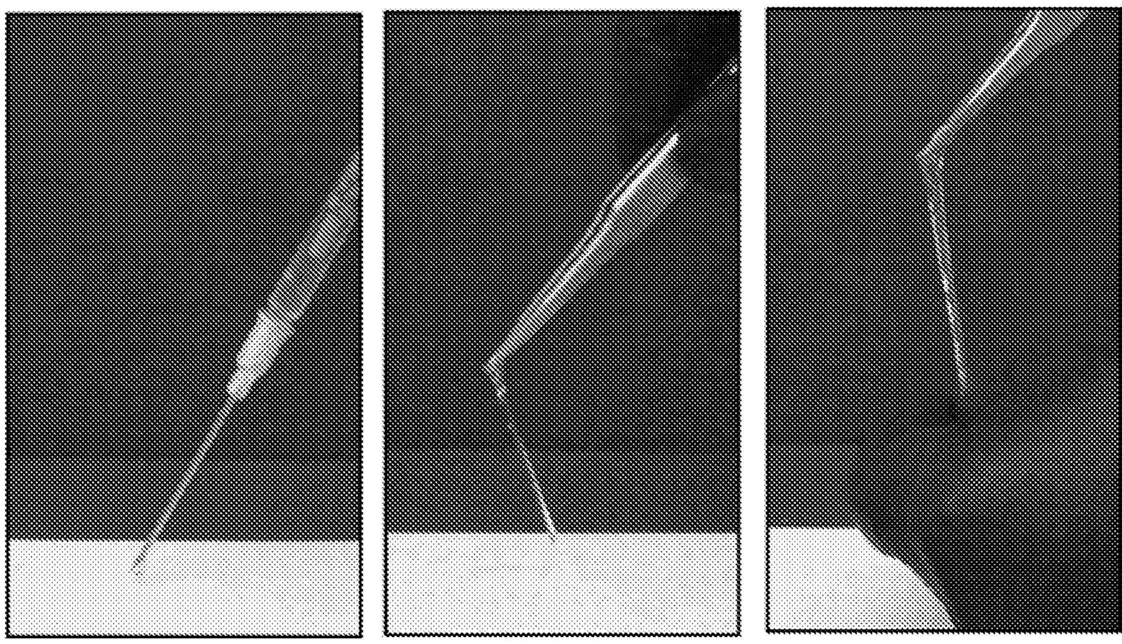
FIG. 3
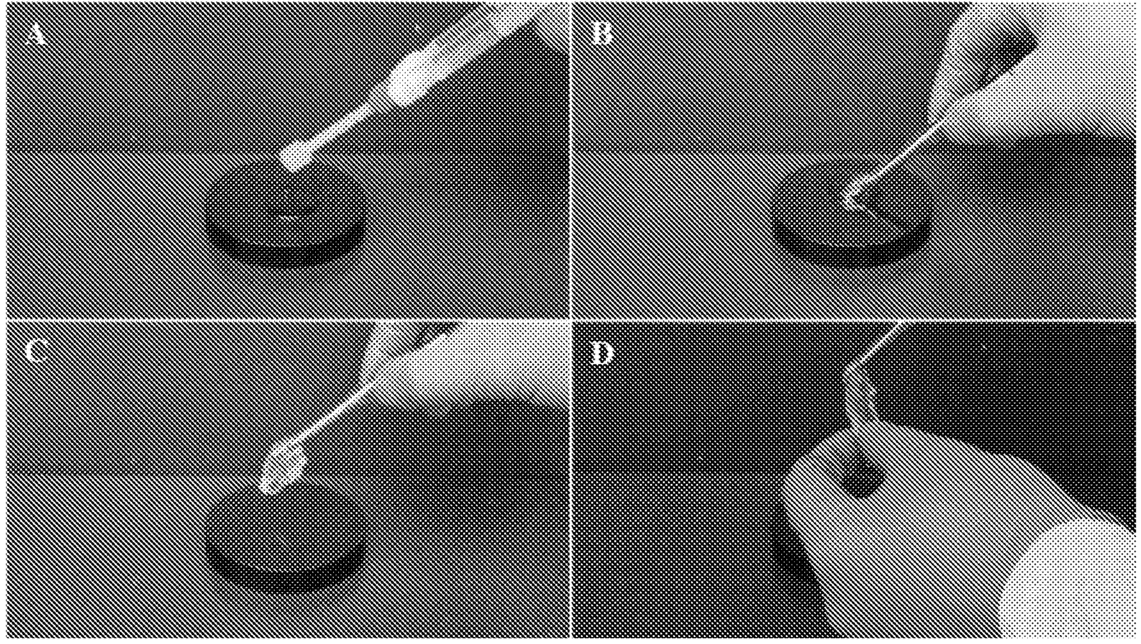
FIGS. 4A-AD

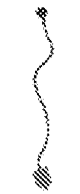

linear (co)polymer with functional chain-end

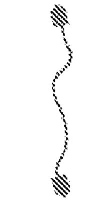

linear (co)polymer with functional chain-ends

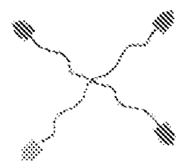

multi-arm (miktoarm) (co)polymer with functional groups

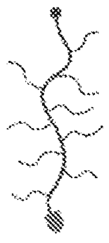

brush-like (co)polymer with functional chain-end

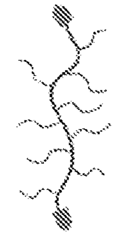

brush-like (co)polymer with functional chain-ends

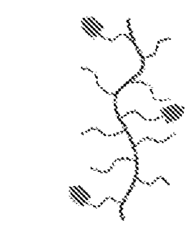

brush-like (co)polymer with functional side-chains

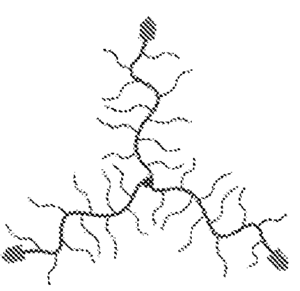

3-arm brush-like polymer with functional chain-ends

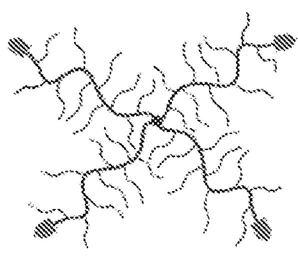

4-arm brush-like polymer with functional chain-ends

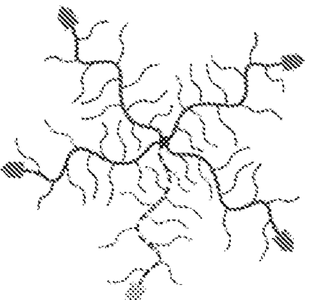

multi-arm (miktoarm) star-like (co)polymer with functional side-chains and/or chain-ends

FIG. 5B

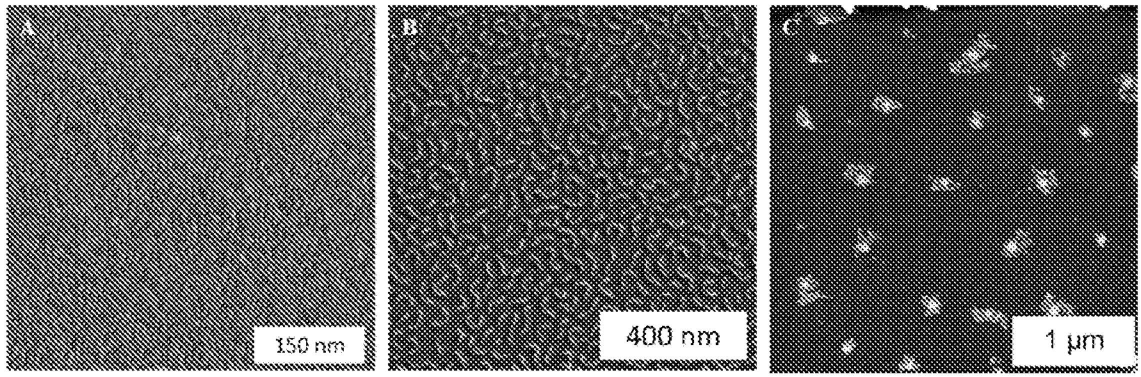
FIGS. 6A-6B
a
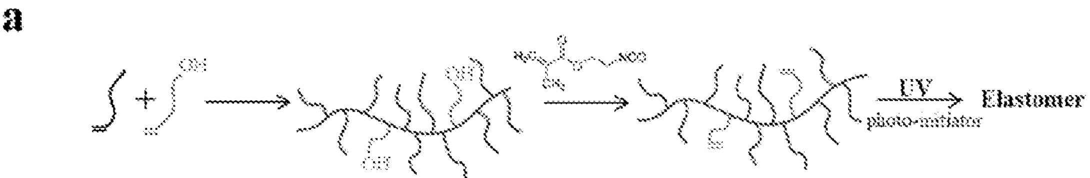
b
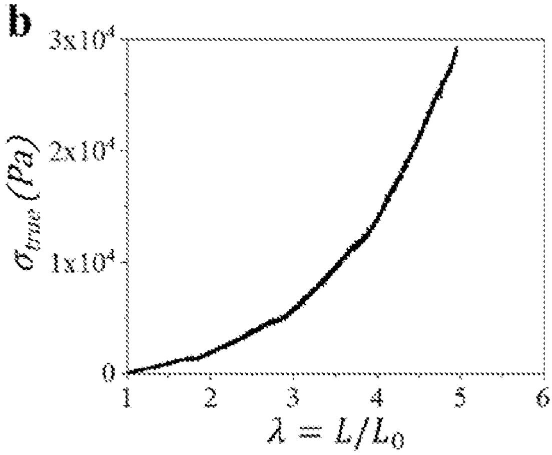
FIGS. 7A-7B b

| G′, G″ | T°C | $\tau_g$ (h) | $\tau_e$ (h) |
|---|---|---|---|
| ■, □ | 37 | 11 | >100 |
| ●, ○ | 60 | 3.2 | >70 |
| ▲, △ | 80 | 1.5 | >15 |

a b (a) Functional bottlebrush (b) Crosslinker

Brush/Comb Network

Brush-on-Brush/Comb Network

INJECTABLE AND MOLDABLE TISSUE-MIMETIC ELASTOMERS AND METHODS RELATED THERETO

CROSS-REFERENCE TO RELATED APPLICATIONS

This Application is a U.S. national phase application under 35 U.S.C. § 371 of International Application No. PCT/US2020/054022, filed on Oct. 2, 2020, which claims the benefit of U.S. Provisional Application No. 62/910,089, filed on Oct. 3, 2019, the contents of which are incorporated herein by reference in their entireties.

STATEMENT REGARDING FEDERALLY SPONSORED RESEARCH

This invention was made with Government support under Grant Nos. DMR-1407645, DMR-1921835, and DMR-2004048 awarded by National Science Foundation. The Government has certain rights in the invention.

BACKGROUND

Injectable implants are attractive alternative to invasive deployment of bulky implants, offering improved patient comfort, reduced surgery costs, faster recovery from surgery, and minimal surgical and post-surgical complications. However, development of safe injectable implants that allow mimicking mechanical properties (softness and firmness) of biological tissues in a single-component material remains challenging. Previously, the only viable class of injectable materials that offer softness of biological tissues are polymer gels. However, polymeric gels contain liquid fraction that can leak into the body over time and upon deformation, thereby releasing toxic chemicals or heavy metals, which are left over from the manufacturing process. Further, soft polymeric gels are fragile materials that undergo fragmentation and migration inside the living and moving body. The most important drawbacks of gel-based implants are leaching of diluent molecules into the body, migration inside the body, mismatch with tissue mechanics, and potential swelling in bodily fluids. Another disadvantage is highly invasive surgery: implantation of bulky implants requires large incision, which is painful for a patient, increases the healing time, and cause permanent scars. This made injectable materials increasingly popular for aesthetic and reconstructive medical applications like dermal fillers to correct age-related folds and wrinkles, as well as post-surgical or post-traumatic soft tissue augmentation. Although the general appeal for injectable implants is constantly increasing, controversies about their safety, efficacy, and long-term side-effects increase concurrently. For example, silicone, one of the most widely used materials in body implants, causes significant safety concerns due to uncontrolled leaching of toxic chemicals and heavy metals as left over from the manufacturing process causing substantial and long-term health risks. In addition to altering gel mechanical properties, leaching instigates inflammatory responses and can cause various diseases, including autoimmune diseases, such as scleroderma, rheumatoid arthritis, and lupus. Polyacrylamide hydrogels is another example of injectable materials used for noninvasive body reconstruction, correction, augmentation, and countering. After injection, these materials remain fluid and thus are prone to various types of displacements inside the body, which required reoperation involving complex invasive procedures such as gel removal, debridement, and tissue reconstruction.

Accordingly, there remains a need for materials and methods that can be administered and maintained safely. Elastomers and related methods disclosed herein can be administered in liquid form followed by formation of a solid implant which does not flow, does not leak, and mimics mechanical properties of biological tissue. Injection can be administered either directly into/onto the body or into a pre-fabricated lumen depending on application. These needs and others are met by the disclosure herein.

SUMMARY

In accordance with the purpose(s) of the invention, as embodied and broadly described herein, the invention, in one aspect, relates to elastomers and related methods that can be useful in, for example, implants with mechanical properties of soft tissue(s).

Disclosed are elastomers formed by crosslinking a first polymer formulation, a substantially solvent-free first polymer formulation, or a first solvent-free polymer formulation comprising a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly (propylene fumarate), a poly(glycerol sebacate), a poly (ethylene terephthalate), a polycarbonate, a polyamide, a polystyrene, or a poly(tetrafluoroethylene), or a combination, or copolymer thereof.

Also disclosed is a method comprising the steps of administering a first polymer formulation, a substantially solvent-free first polymer formulation, or a first liquid solvent-free polymer formulation into a tissue or onto a surface of a tissue of a subject, and crosslinking the first polymer formulation, the substantially solvent-free first polymer formulation, or the first liquid solvent-free polymer formulation, thereby forming an elastomer inside the tissue or onto the surface of the tissue of the subject.

Also disclosed herein is a kit comprising a first container comprising a first compartment comprising a first polymer formulation, a substantially solvent-free first polymer formulation, or a first liquid solvent-free polymer formulation capable of crosslinking and forming an elastomer when administered into a tissue or onto a surface of a tissue of a subject; and a sterile administration device.

Also disclosed herein is a dual-chamber syringe comprising a first chamber containing a first polymer formulation, a substantially solvent-free first polymer formulation, or a first liquid solvent-free polymer formulation; a second chamber containing a second polymer formulation, a substantially solvent-free second polymer formulation, or a second liquid solvent-free polymer formulation capable of crosslinking with the first polymer formulation, the substantially solvent-free first polymer formulation, or the first liquid solvent-free polymer formulation and forming an elastomer when administered into a tissue or onto a surface of a tissue of a subject; a plunger configured to simultaneously depress within the first chamber and the second chamber; and a needle in fluid communication with the first chamber and the second chamber, wherein the first chamber and second chamber are configured to deliver through the needle an amount of the first polymer formulation, the substantially solvent-free first polymer formulation, or the first liquid solvent-free polymer formulation and an amount the second polymer formulation, the substantially solvent-free second polymer formulation, or the second polymer formulation, the substantially solvent-free second polymer formulation, or the second liquid solvent-free polymer formulation when the plunger is depressed.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 3 demonstrates solvent-free injection with a single-chamber syringe and curing of injectable formulations into elastomers with tissue-mimetic mechanical properties. The syringe chamber contains a pre-mixed composition of functionalized bottlebrushes and crosslinker as described in FIG. 8.

FIGS. 4A-D demonstrates administration of injectable elastomers: (4A) double-syringe injection, (4B) curing at room temperature, (4C) handling, and (4D) super-soft tissue-mimetic mechanics.

FIG. 5B shows the macromolecular toolbox of linear and brush/comb-like (co) polymers with different architectures to design disclosed injectable and moldable tissue mimetic elastomers. Each item in the macromolecular toolbox can play one or multiple roles including but not limited to diluent, crosslinker, plasticizer, tackifier, or water uptake agent. It is obvious that the injectable and moldable tissue mimetic elastomer formulations can also contain predetermined amounts of other ingredients including but not limited to small molecule crosslinkers, catalysts, solvents, drugs, (bio) ceramics, magnetic powder, nano/microparticles and proteins.

FIGS. 6A-C shows atomic force microscopy (AFM) of brush polymers. Height micrographs of PDMS-r-PEG bottlebrushes deposited on mica by Langmuir-Blodget technique for PDMS (6A) linear bottlebrush, $n_{sc}$14, (6B) linear bottlebrush, $n_{sc}$70, and (6C) multi-arm (star-like), $n_{sc}$14. $n_{bb}$ is determined as $L_n/l_0$, where $L_n$ is number average measured bottlebrush contour length via AFM and $l_o$=0.25 nm is the length of bottlebrush backbone monomeric unit. Bottlebrush dispersity, Đ=$M_w/M_n$ is calculated from analysis of >300 molecules.

FIGS. 7A-B shows (7*a*) exemplary synthesis, and (7*b*) mechanical properties of a single-component photo-curable injectable, solvent-free, non-leachable, and tissue-mimetic elastomer.

FIGS. 26A and 4B Shows an exemplary synthesis of dual-component slow-cure injectable tissue-mimetic elastomers composed of (26A) random polydimethylsiloxane-poly(ethylene glycol) (PDMS-r-PEG) brush polymers with a controlled fraction of end-functionalized side-chains, and (26B) a linear difunctional crosslinker.

$$Conv_{PDMS} = ([\text{Area}(a+a')/68.2] - [\text{Area}(d)/1])/[\text{Area}(a+a')/68.2] = 79\%.$$

$$n_{bb} = Conv_{PDMS} * \frac{[M]}{[I]} = 79\% * 1125 = 889.$$

Figure 28:
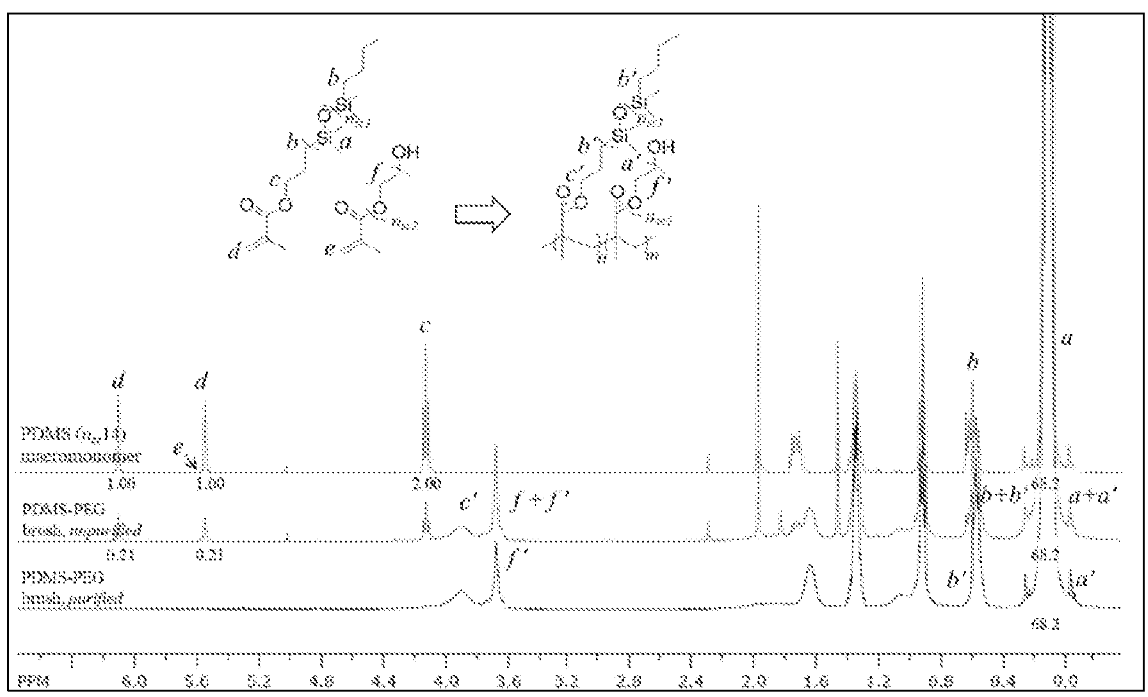

FIG. 28 shows $^1$H-NMR of random polydimethylsiloxane-poly(ethylene glycol) brushes (PDMS-r-PEG, n:m, 95:5, $n_{sc1}$: 14, $n_{sc2}$: 12) at different stages of synthesis (400 MHz, $CDCl_3$): 6.16, 5.57 ($CH_2{=}C(CH_3)C{=}O$, PDMS macromonomer, s, 1H), 4.12 (CO—$OCH_2$—, PDMS macromonomer, t, 2H), 3.91 (CO—$OCH_2$—, PDMS brush, t, 2H), 3.78 (CO—$OCH_2$—, PEG brush, t, 2H), 3.67 (—$OC_2H_4O$—, PEG brush, m, 32H), 0.55 (—$CH_2$—$(Si(CH_3)_2—O)_n$—$CH_2$—$CH_2$—, PDMS macromonomer and brush mixture, m, 4H), 0.09 (—$(Si(CH_3)_2—O)_n$—, PDMS macromonomer and brush mixture, s, 68.2H).

Figure 29:
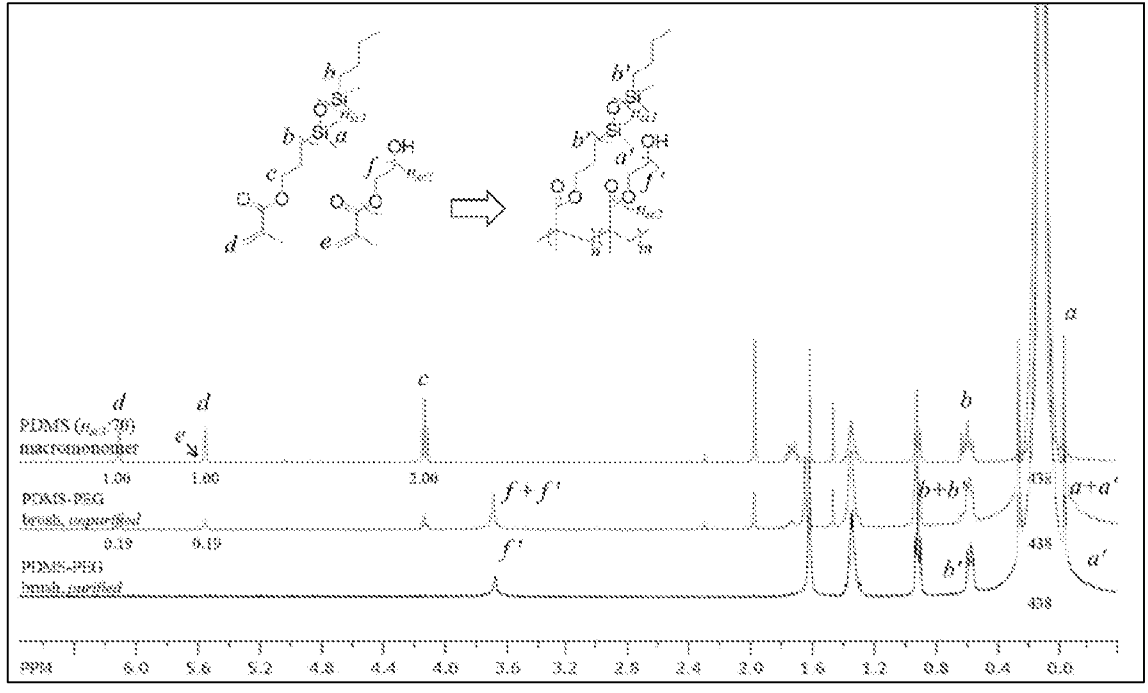

FIG. 29 shows $^1$H-NMR of random polydimethylsiloxane-poly(ethylene glycol) brushes (PDMS-r-PEG, n:m, 95:5, $n_{sc1}$: 70, $n_{sc2}$: 12) at different stages of synthesis (400 MHz, $CDCl_3$): 6.16, 5.57 ($CH_2{=}C(CH_3)C{=}O$, PDMS macromonomer, s, 1H), 4.12 (CO—$OCH_2$—, PDMS macromonomer, t, 2H), 3.91 (CO—$OCH_2$—, PDMS brush, t, 2H), 3.78 (CO—$OCH_2$—, PEG brush, t, 2H), 3.67 (—$OC_2H_4O$—, PEG brush, m, 32H), 0.55 (—$CH_2$—$(Si(CH_3)_2—O)_n$—$CH_2$—$CH_2$—, PDMS macromonomer and brush mixture, m, 4H), 0.09 (—$(Si(CH_3)_2—O)_n$—, PDMS macromonomer and bottlebrush mixture, s, 438H). Peak c' for brushes with $n_{sc1}$: 70 do not show on NMR in $CDCl_3$ in contrast to $n_{sc3}$: 14 brushes.

$$Conv_{PDMS} = ([\text{Area}(a+a')/438] - [\text{Area}(d)/1])/[\text{Area}(a)/438] = 81\%.$$

$$n_{bb} = Conv_{PDMS} * \frac{[M]}{[I]} = 81\% * 375 = 304.$$

Figure 30:
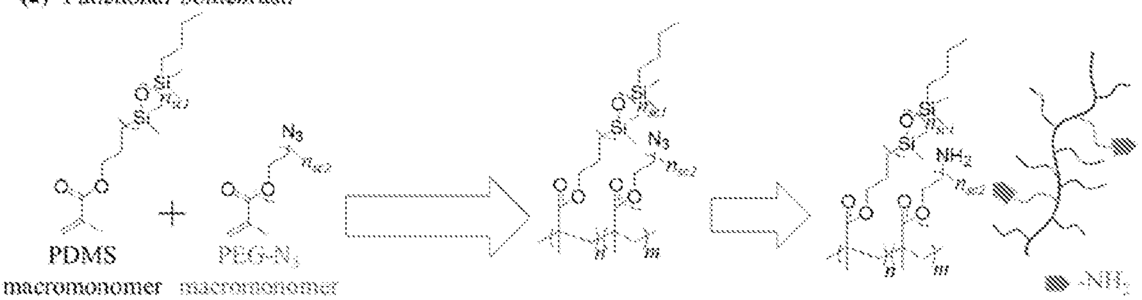

FIG. 30 shows exemplary synthesis of dual-component fast-cure injectable tissue-mimetic elastomers composed of random polydimethylsiloxane-poly(ethylene glycol) (PDMS-r-PEG.$N_3$) brush polymers with a controlled fraction of end-functionalized side-chains and a linear difunctional crosslinker.

Figure 31:
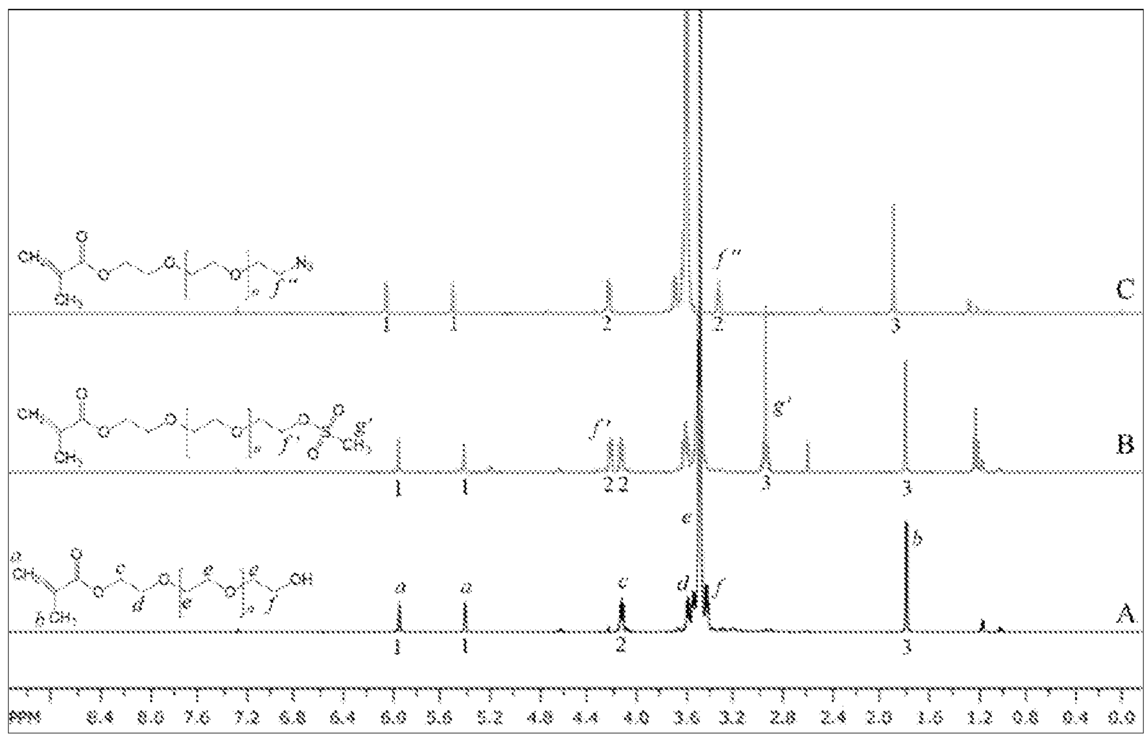

FIG. 31 shows $^1$H-NMR of poly(ethylene glycol) macromonomer functionalization at different stages. (A) poly (ethylene glycol) (PEG) macromonomer (400 MHz, $CDCl_3$): 5.98, 5.41 ($CH_2$=C($CH_3$)C=O, s, 1H), 4.15 (CO—$OCH_2$—, t, 2H), 3.59 (CO—$OCH_2$—$CH_2O$—, t, 2H), 3.48 (—$OC_2H_4O$—, m, 32H), 3.42 (—$CH_2OH$, t, 2H), 1.8 ($CH_2$=C($CH_3$)C=O, s, 3H). (B) PEG macromonomer after mesylation reaction (400 MHz, $CDCl_3$): 5.98, 5.41 ($CH_2$—C($CH_3$)C=O, s, 1H), 4.22 (—$CH_2OSO_2CH_3$, t, 2H), 4.15 (CO—$OCH_2$—, t, 2H), 3.59 (CO—$OCH_2$—$CH_2O$—, t, 2H), 3.48 (—$OC_2H_4O$—, m, 32H), 2.96 (—$CH_2OSO_2CH_3$, s, 3H), 1.8 ($CH_2$=C($CH_3$)C=O, s, 3H). (C) azide-terminated PEG macromonomer (400 MHZ, $CDCl_3$): 6.05, 5.52 ($CH_2$=C($CH_3$)C=O, s, 1H), 4.21 (CO—$OCH_2$—, t, 2H), 3.68 (CO—$OCH_2$—$CH_2O$—, t, 2H), 3.60 (—$OC_2H_4O$—, m, 32H), 3.37 (—$CH_2N_3$, t, 2H), 1.90 ($CH_2$=C($CH_3$)C=O, s, 3H).

Figure 32:
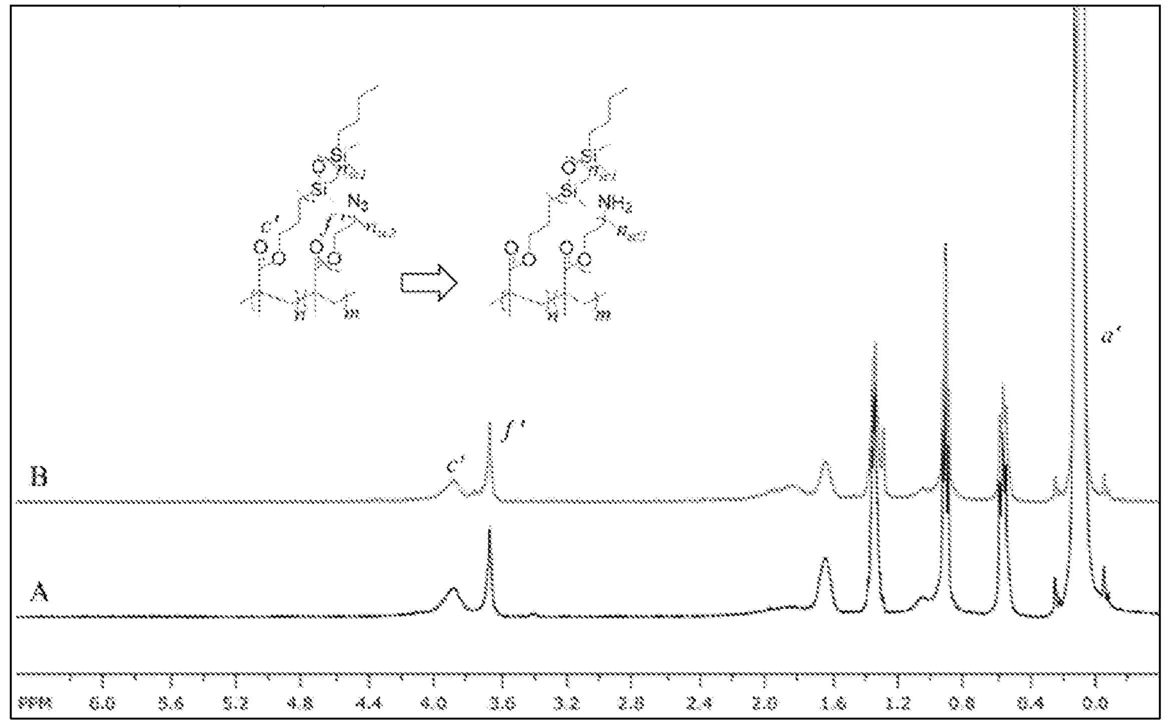

FIG. 32 shows $^1$H-NMR (400 MHZ, $CDCl_3$) of (A) random polydimethylsiloxane/azide-terminated poly(ethylene glycol) (PDMS-r-PEG.$N_3$), and (B) random polydimethylsiloxane/amine-terminated poly(ethylene glycol) (PDMS-r-PEG.$NH_2$ bottlebrush copolymers.

Figure 33:
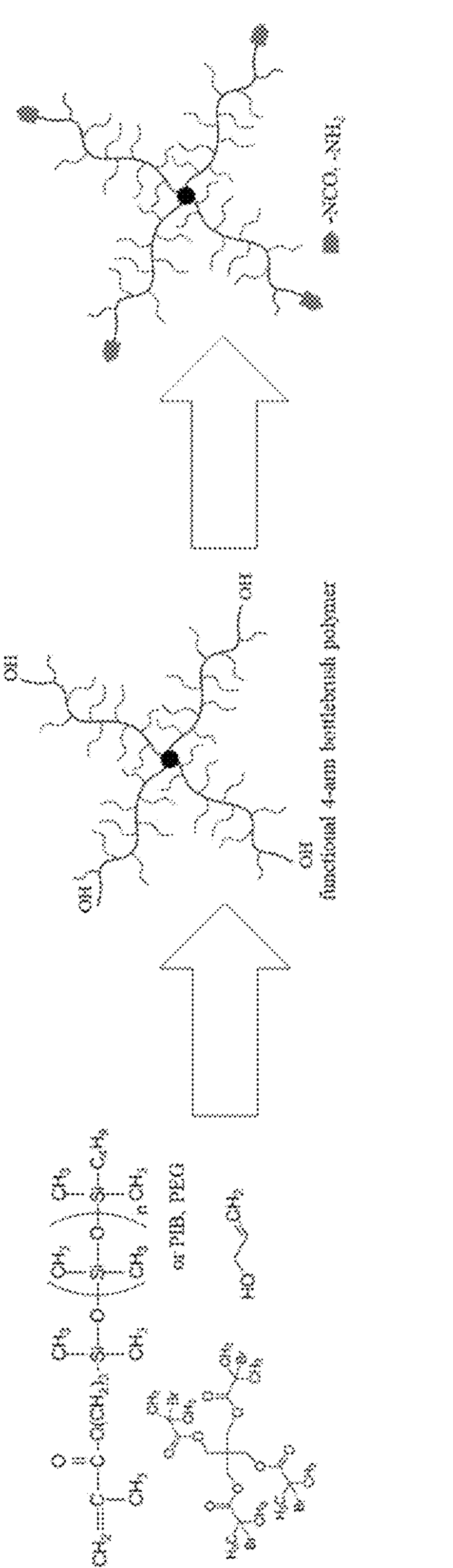

FIG. 33 shows a representative schematic illustrating monomethacryloxypropyl-terminated poly(dimethylsiloxane) as the as the brush like polymer to be terminated with allyl alcohol. Subsequently, either part or all hydroxyl end groups can be substituted with a crosslink moiety, e.g., isocyanate or amine groups.

Figure 34B:
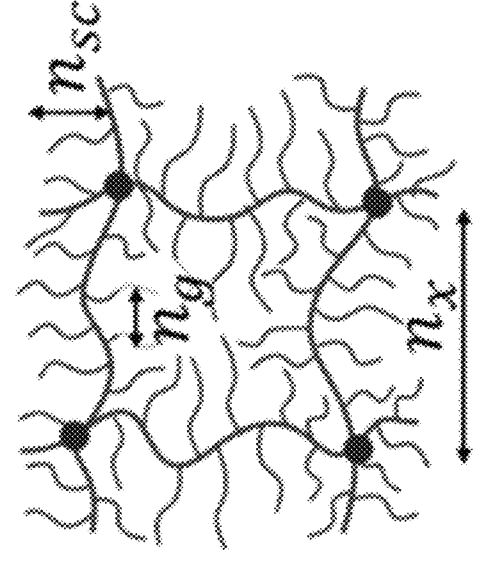
Figure 34A:
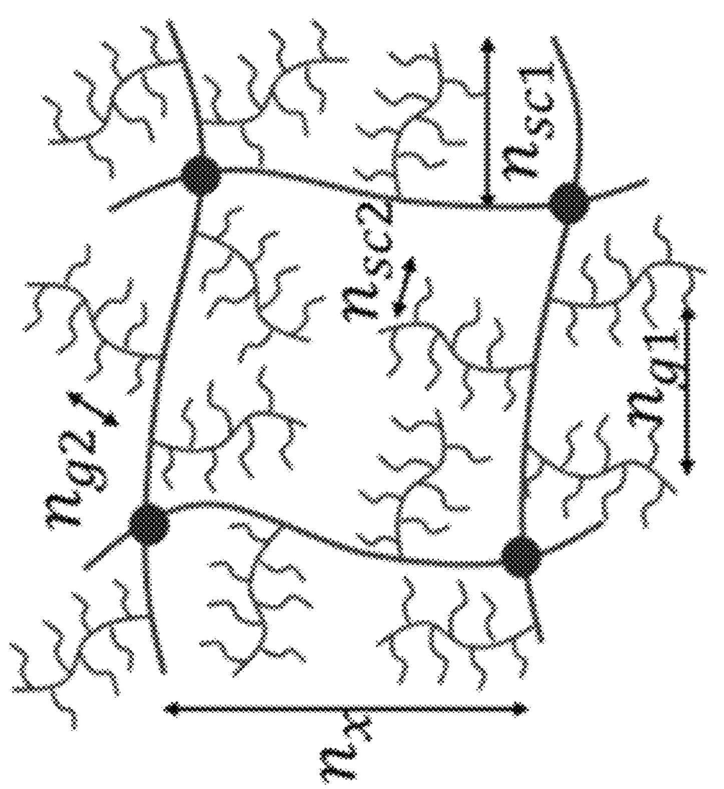

FIG. 34A and FIG. 34B show a schematic representation of brush-on-brush/comb (FIG. 34A) and brush/comb (FIG. 34B) network architectures of injectable and moldable tissue-like elastomers.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. DEFINITIONS

The present invention now will be described more fully hereinafter with reference to the accompanying drawings, in which illustrative aspects of the invention are shown. In the drawings, the relative sizes of regions or features may be exaggerated for clarity. This invention may, however, be embodied in many different forms and should not be construed as limited to the aspects set forth herein; rather, these aspects are provided so that this disclosure will be thorough and complete, and will fully convey the scope of the invention to those skilled in the art.

The disclosures of all patent references cited herein are hereby incorporated by reference to the extent they are consistent with the disclosure set forth herein. As used herein in the description of the invention and the appended claims, the singular forms "a," "an," and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular aspects only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that in various aspects of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measureable value may include any other range and/or individual value therein.

As used herein, "polymer network" refers to a polymer in which covalent cross-linking or non-covalent cross-linking (e.g., via chain entanglements, hydrogen bonding, or microphase separation) has occurred. Examples of polymer networks include, but are not limited to, polymer gels and elastomers.

As used herein, "polymer" refers to the product of a polymerization reaction in which one or more (macro) monomers are linked together. A polymer includes both homopolymers and copolymers. Additionally, a polymer can be linear, brush-like, crosslinked, or a mixture thereof.

As used herein, "homopolymer" refers to a polymer resulting from the polymerization of a single (macro)monomer.

As used herein, "copolymer" refers to a polymer resulting from the polymerization of two or more chemically distinct (macro)monomers.

As used herein, "linear polymer" refers to a polymer having side chains that are shorter than the spacer between neighboring side chains along the backbone or main chain of the polymer. When the spacer is negligibly short, "linear polymer" refers to a polymer having side chains that are shorter than the persistence length of the side chains. For example, a polymer chain with side chains, in which the spacer consists of two covalent bonds and side chain persistence length is ten covalent bonds long, is considered as a "linear polymer." Examples of linear polymers include, but are not limited to, vinyl polymers with relatively short side chains or small side groups. When the side chains become longer than their persistence length, the polymer is no longer considered a linear polymer. Rather, the polymer is now considered a brush-like polymer as further detailed below. For example, poly(butyl acrylate) with n-butyl side groups is a linear polymer whereas poly(octadecyl acrylate) with n-octadecyl side chains is a brush-like polymer.

As used herein, "comb-like polymer block" refers to a brush-like polymer block in which the spacer length is significantly shorter than the side chain contour length, yet it is longer than the square-root of the side chain length. For example, a comb-like polymer block could have poly(butyl acrylate) side chains with a degree of polymerization of 100 separated by a poly(butyl acrylate) spacer with a degree of polymerization of 30 (30<<100).

As used herein, "bottlebrush-like polymer block" refers to a polymer block having side chains that are significantly longer than the spacer between neighboring side chains along the backbone or main chain of the polymer. Thus, without wishing to be bound by theory, the side chains can be at least more than two monomeric units long, more than 3 monomeric units long, more than 4 monomeric units long, more than 5 monomeric units long, more than 6 monomeric units long, more than 7 monomeric units long, or more than 8 monomeric units long, so long as the spacer is shorter than the square-root of the side chain length. For example, a bottlebrush-like polymer block could have poly(butyl acrylate) side chains with a degree of polymerization of 100 separated by a poly(butyl acrylate) spacer with a degree of polymerization of 2 (2<<10=sqrt (100)).

As used herein, "amorphous" refers to a state of matter that is not crystalline, i.e., that has no lattice structure that is characteristic of a crystalline state. Thus, in various aspects, a polymer block can be at least 1% amorphous, at least 5% amorphous, at least 10% amorphous, at least 15% amorphous, at least 20% amorphous, at least 30% amorphous, at least 40% amorphous, at least 50% amorphous, at least 60% amorphous, at least 70% amorphous, at least 80% amorphous, at least 90% amorphous, or even at least 99% amorphous. Without wishing to be bound by theory, an amorphous block enables better control of network structure and network formation process via microphase separation.

As used herein, "binding functionality" refers to a chemical group capable of binding polymer blocks, e.g., linear polymer blocks. In various aspects, a binding functionality is capable of covalently binding polymer blocks; however, non-covalent binding (e.g., via hydrogen bonds, ionic bonds, metal-ligand and Van der Waals forces) are also envisioned. Examples of binding functionalities include, but are not limited to maleimide moieties, vinyl moieties, acrylate moieties, methacrylate moieties, hydroxyl moieties, aldehyde moieties, isocyanate moieties, amino moieties, carboxylic acid moieties, alkoxy moieties, oxime moieties, acetoxy moieties, amide moieties, diene moieties, dienophile moieties, alkyne moieties, azide moieties, thiol moieties, urea moieties, catechol moieties, Guaiacol moieties, and furan moieties.

As used herein, "elastic modulus" refers to the degree of stiffness of a polymer network. Thus, in various aspects, a polymer network has an elastic modulus of less than about $10^9$ Pa, less than about $10^8$ Pa, less than about $10^7$ Pa, less than about $10^6$ Pa, less than about $10^5$ Pa, or less than about $10^4$ Pa, or less than about $10^3$ Pa, or from about $10^2$ Pa to about $10^9$ Pa, or from about $10^2$ Pa to about $10^6$ Pa.

As used herein, "strain stiffening parameter" refers to the ability of a polymer network to increase its stiffness (i.e., increase in the polymer network's elastic modulus) during deformation. The "strain stiffening parameter" can also be called the "firmness parameter," which characterizes the ability of a soft material to resist deformation.

As used herein, "reversible molding" refers to the ability of a polymer network to make a shape and then disassemble that shape, if needed, followed by re-assembly into a different shape. Without wishing to be bound by theory, molding can be done from solution state or from melt state.

As used herein, "biocompatible" refers to materials that are not unduly reactive or harmful to a subject upon administration.

As used herein, a "liquid solvent-free polymer formulation" refers to a liquid polymer formulation that contains no measurable amount of solvent, such as a biologically acceptable solvent.

As used herein, a "substantially solvent-free liquid polymer formulation" refers to a liquid polymer formulation that containing less than 20 wt % of a solvent, such as a biologically acceptable solvent. For example, the "substantially solvent-free liquid polymer formulation" can contain less than 15 wt %, 10 wt %, 7.5 wt %, 5 wt %, 4 wt %, 3 wt %, 2 wt %, 1 wt %, 0.5 wt %, 0.25 wt %, 0.1 wt %, 0.05 wt %, or 0.001 wt % of a solvent, such as a biologically acceptable solvent.

B. ELASTOMERS

The elastomers disclosed herein can be administered topically, subcutaneously, or non-invasively onto tissues and/or into hard-to-reach body parts. The elastomers are formed from a polymer formulation, a substantially solvent-free polymer formulation, or a solvent-free polymer formulation that is administered onto the surface of tissue or into tissue as a liquid followed by in-situ curing. The polymer formulations that becomes the elastomers disclosed herein can have the following advantages: (i) solvent-free administration (fluid at ambient conditions), (ii) in-situ curing (become an elastomer when injected into/onto the body), (iii) tunable curing duration at physiological conditions, (iv) tunable mechanical properties of final implant matching that of surrounding tissue, (v) non-leaching composition (safe and invariant over time), and (vi) minimal or none side products of the curing process/reaction (safety), (vii) capability of decupling mechanical properties and curing time, (viii) moldability and forming into complex geometries by means of different techniques including but not limited to additive manufacturing techniques (e.g., 3D-printing).

Depending on application of the elastomers, such as breast implants, dermal fillers, or tissue fixation, the disclosed materials can be controlled such that the curing time is from seconds to weeks. Depending on targeted tissue, the developed formulations allow fine tuning of the Young's modulus from $10^2$ to $10^6$ Pa, that is from the modulus of adipose tissue to that of skin. The resultant elastomers are solvent-free with a gel fraction up to 98%, which ensures minimal amount of leachables (<2%). For example, resultant elastomers can have a gel fraction of 100%, which ensures no amount of leachables (0%)

Disclosed herein is a platform for injectable elastomers, such as substantially solvent-free injectable elastomers or solvent-free injectable elastomers that replicate mechanical profiles (i.e., the unique combination of softness and firmness) of tissue, such as soft tissues. The developed methodology relies on synthesis of functionalized polymers, such as brush-like polymer (combs and bottlebrushes) and block copolymers (combination of brush and linear blocks), that are initially liquid and then crosslink into elastomers when administered onto a tissue surface or into tissue. After crosslinking, the final product (implant) is non-leachable and mimics and matches mechanics of the surrounding tissue.

In one aspect, disclosed herein is a polymer formulation, such as a first polymer formulation or a second polymer formulation. In another aspect, disclosed herein is a substantially solvent-free polymer formulation, such as a substantially solvent-free first polymer formulation or a substantially solvent-free second polymer formulation. In yet another aspect, disclosed herein is a solvent-free polymer formulation, such as a solvent-free first polymer formulation or a solvent-free second polymer formulation.

Disclosed herein are elastomers formed by crosslinking a first polymer formulation, a substantially solvent-free first polymer formulation, or a first solvent-free polymer formulation comprising a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly (propylene fumarate), a poly(glycerol sebacate), a poly (ethylene terephthalate), a polycarbonate, a polyamide, a polystyrene, or a poly(tetrafluoroethylene), or a combination, or copolymer thereof. For example, the first polymer formulation, the substantially solvent-free first polymer formulation, or the first solvent-free polymer formulation can comprise a polysiloxane or a polyolefin comprising polyisobutylene, polyisoprene, polybutadiene, or combination, or copolymer thereof.

In one aspect, the elastomer is formed by crosslinking a first cross-link moiety on a polymer in the first polymer formulation, the substantially solvent-free first polymer formulation, or the first solvent-free polymer formulation with an identical first cross-link moiety on the polymer in the first polymer formulation, the substantially solvent-free first polymer formulation, or the first solvent-free polymer formulation, thereby forming the elastomer. In one aspect, the first cross-link moiety is an isocyanate, amine, aldehyde, diene, dienophile, epoxide, cyanoacrylate, thiol, catechol, oligonucleotide, hydrogen bond donor/acceptor group, alkyne, alkoxy, azide, vinyl, acrylate, methacrylate, or hydroxyl group.

It is understood that the cross-link moieties disclosed herein are selected to be compatible with each other for cross-linking. It is also understood that the cross-linking can occur spontaneously or with stimuli. For example, photo initiation can be used to crosslink a double bond or hydroxyl groups.

For example, the first cross-link moiety can be an isocyanate group, which can be cross-linked to amine group. In this case, the curing duration is controlled by the reactivity of isocyanate group.

In one aspect, the elastomer is formed by crosslinking a second cross-link moiety on a polymer in the first polymer formulation, the substantially solvent-free first polymer formulation, or the first solvent-free polymer formulation with a third cross-link moiety on the polymer in the first polymer formulation, the substantially solvent-free first polymer formulation, or the first solvent-free polymer formulation, thereby forming the elastomer. In one aspect, each of the second cross-link moiety and the third cross-link moiety is hydrogen bond donor/acceptor groups, ureidopyrimidinone, maleimide, catechol, guaiacol, thiol, oligonucleotide, cyanoacrylate, amine, alkyne, azide, vinyl, acrylate, methacrylate, isocyanate, aldehyde, hydroxyl, epoxide, oxime, alkoxy, acetoxy, diene, or a dienophile group thereof.

For example, the second cross-link moiety can be an amine group, and the third cross-link moiety can be an aldehyde group. In another example, the second cross-link moiety can be an amine or hydroxyl group, and the third cross-link moiety can be an isocyanate group. In yet another example, the second cross-link moiety can be an azide group, and the third cross-link moiety can be an alkyne group. In yet another example, the second cross-link moiety can be a double bond (e.g., methacrylate group), and the third cross-link moiety can be a hydroxyl group. In yet another example, the second cross-link moiety can be a diene group, and the third cross-link moiety can be a dienophile group.

In one aspect, the elastomer is formed by crosslinking the first polymer formulation, the substantially solvent-free first polymer formulation, or the first solvent-free polymer formulation with a second polymer formulation, a substantially solvent-free second polymer formulation, or a second liquid solvent-free polymer formulation to form comprising a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly(propylene fumarate), a poly(glycerol sebacate), a poly(ethylene terephthalate), a polycarbonate, a polyamide, a polystyrene, or a poly(tetrafluoroethylene), or a combination, or copolymer thereof.

In one aspect, the second polymer formulation, the substantially solvent-free second polymer formulation, or the second liquid solvent-free polymer formulation contains a polymer that acts as a linker between polymers in the first polymer formulation, the substantially solvent-free first polymer formulation, or the first solvent-free polymer formulation.

In one aspect, the elastomer is formed by crosslinking a fourth cross-link moiety on a polymer in the first polymer formulation, the substantially solvent-free first polymer formulation, or the first solvent-free polymer formulation with a fifth cross-link moiety on a polymer in the second polymer formulation, the substantially solvent-free second polymer formulation, or the second liquid solvent-free polymer formulation, thereby forming the elastomer. In one aspect, the fourth cross-link moiety and the fifth cross-link moiety is hydrogen bond donor/acceptor groups, ureidopyrimidinone, maleimide, catechol, guaiacol, thiol, oligonucleotide, cyanoacrylate, amine, alkyne, azide, vinyl, acrylate, methacrylate, isocyanate, aldehyde, hydroxyl, epoxide, oxime, alkoxy, acetoxy, diene, or a dienophile group.

For example, the fourth cross-link moiety can be an amine group, and the fifth cross-link moiety can be an aldehyde group. In another example, the fourth cross-link moiety can be an amine or hydroxyl group, and the fifth cross-link moiety can be an isocyanate group. In yet another example, the fourth cross-link moiety can be an azide group, and the fifth cross-link moiety can be an alkyne group. In yet another example, the fourth cross-link moiety can be a methacrylate group, and the fifth cross-link moiety can be a hydroxyl group. In yet another example, the fourth cross-link moiety can be a diene group, and the fifth cross-link moiety can be a dienophile group.

In one aspect, the liquid formulations, substantially solvent-free formulations, or liquid solvent-free polymer formulations disclose herein can comprise neutral macromonomers copolymerized with a controlled fraction of macromonomers containing functional end-groups, from 0.1-100 mol. %, for example by using controlled atom transfer radical polymerization (ATRP). In one example, monomethacryloxypropyl-terminated poly(dimethylsiloxane) ($M_n$~1000 g/mol) can be used as the as the brush like polymer and 0.3-5 mol. % of hydroxyl terminated poly(ethylene glycol) methacrylate ($M_n$~500 g/mol) comacromonomer are copolymerized, as shown in the scheme below.

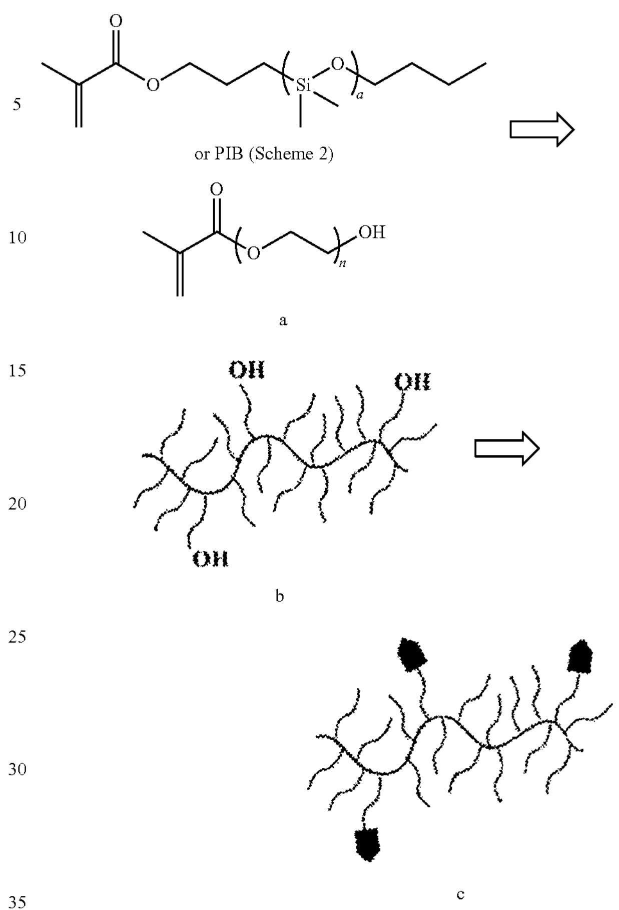

The tune melt viscosity and crosslink density, the degree of backbone polymerization can be controlled within $n_{bb}$=100-2000.

In one aspect, the liquid solvent-free polymer formulations disclose herein can comprise multi-arm (star-like) bottlebrush or comb polymers containing functional end-(terminal) groups on the backbone, from 0.1-20 mol. %, for example by using controlled polymerization techniques. In one example, monomethacryloxypropyl-terminated poly(dimethylsiloxane) ($M_n$~1000 or 5,000 or 10,000 g/mol) can be used as the as the brush like polymer to be terminated with allyl alcohol, as shown in FIG. 33. Subsequently, either part or all hydroxyl end groups can be substituted with a cross-link moiety, e.g., isocyanate or amine groups (see FIG. 33). Both melt viscosity and crosslink density can be finely controlled through degree of backbone polymerization and number of arms, as shown and described herein.

In one aspect, the first polymer formulation, the substantially solvent-free first polymer formulation, or the first solvent-free polymer formulation comprises a polymer having a brush-like structure.

In one aspect, the second polymer formulation, the substantially solvent-free second polymer formulation, or the second liquid solvent-free polymer formulation comprises a polymer having a brush-like structure.

In a further aspect, the elastomer has an elastic modulus from about $10^2$ Pa to about $10^6$ Pa. In a still further aspect, the elastomer has an elastic modulus from about $10^2$ Pa to about $10^4$ Pa. In a still further aspect, the elastomer has an elastic modulus from about $10^4$ Pa to about $10^6$ Pa. In a still further aspect, the elastomer has an elastic modulus from about $10^3$ Pa to about $10^5$ Pa.

In a further aspect, the elastomer has an elastic modulus from about $10^2$ Pa to about $10^6$ Pa at a temperature of greater than about 90° F. In a still further aspect, the elastomer has an elastic modulus from about $10^2$ Pa to about $10^4$ Pa at a temperature of greater than about 90° F. In a still further aspect, the elastomer has an elastic modulus from about $10^4$ Pa to about $10^6$ Pa at a temperature of greater than about 90° F. In a still further aspect, the elastomer has an elastic modulus from about $10^3$ Pa to about $10^5$ Pa at a temperature of greater than about 90° F. For example, the temperature can be from about 90° F. to about 110° F., such as from about 90° F. to about 100° F.

In a further aspect, the elastomer has a strain-stiffening parameter of from about 0.1 to about 1. In a still further aspect, the elastomer has a strain-stiffening parameter of from about 0.1 to about 0.9, of from about 0.1 to about 0.8, of from about 0.1 to about 0.7, of from about 0.1 to about 0.6, of from about 0.1 to about 0.5, of from about 0.1 to about 0.4, of from about 0.1 to about 0.3, of from about 0.1 to about 0.2, of from about 0.2 to about 1, of from about 0.3 to about 1, of from about 0.4 to about 1, of from about 0.5 to about 1, of from about 0.6 to about 1, of from about 0.7 to about 1, of from about 0.8 to about 1, of from about 0.9 to about 1, of from about 0.2 to about 0.9, of from about 0.3 to about 0.8, or of from about 0.4 to about 0.7.

In a further aspect, the elastomer can undergo uniaxial elongation from about 2-fold to about 10-fold. In a still further aspect, the elastomer can undergo uniaxial elongation from about 2-fold to about 9-fold, from about 2-fold to about 8-fold, from about 2-fold to about 7-fold, from about 2-fold to about 6-fold, from about 2-fold to about 5-fold, from about 2-fold to about 4-fold, from about 2-fold to about 3-fold, from about 3-fold to about 9-fold, from about 4-fold to about 9-fold, from about 5-fold to about 9-fold, from about 6-fold to about 7-fold, from about 8-fold to about 9-fold, from about 3-fold to about 8-fold, or from about 4-fold to about 7-fold.

In a further aspect, the elastomer can be formed while undergoing reversible molding, injected, or cast into a desired shape. In a further aspect, the elastomer can be formed while being 3D-printed into a desired shape. Desired shapes include, for example, bodily organs.

In one aspect, the formed elastomer does not leach over time. "Does not leach" or "leach free" means that the gel fraction is >98% with <2% that does not leach.

Figure 1:
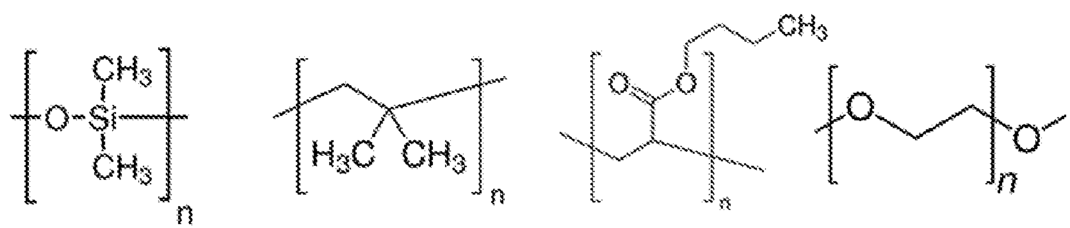
FIG. 1 shows specific non-limiting examples of chemical compositions used for the synthesis of elastomers having a brush-like structure of network strands.

Specific non-limiting examples of elastomers having a brush chemical composition includes poly(dimethyl siloxane) and polyisobutylene, which is shown in FIG. 1. Brush-like architecture of the elastomer dilutes entanglements to independently achieve predetermined stress-strain behavior and extensibility without the complications associated with swollen gels, infinite chain-ends on bottlebrush backbones make it possible to tailor desired networks functionalities (e.g., tissue adhesion, antifouling, (bio) conjugation, strain-adaptive stiffening, and self-healing).

Specific crosslinking moieties for brush-like tissue-mimetic elastomers with different crosslinking strategies are shown in FIGS. 2A-2J.

C. SYRINGE AND KIT

Also disclosed herein is a syringe, such as a single chamber (FIG. 3) or dual chamber syringe (FIGS. 4A-D), comprising the solvent-free polymer formulations disclosed herein. The syringe, such as the dual chamber syringe, can be used to administer to the solvent-free polymer formulations disclosed herein to form an elastomer disclosed herein.

The syringe, such as a dual chamber syringe, disclosed herein can be used in the methods disclosed herein.

The formulations disclosed herein can also be present in a single barrel syringe.

In one aspect, disclosed herein is a dual-chamber syringe comprising a first chamber containing a first polymer formulation, a substantially solvent-free first polymer formulation, or a first solvent-free polymer formulation; a second chamber containing a second polymer formulation, a substantially solvent-free second polymer formulation, or a second liquid solvent-free polymer formulation capable of crosslinking with the first polymer formulation, the substantially solvent-free first polymer formulation, or the first solvent-free polymer formulation and forming an elastomer when administered into a tissue or onto a surface of a tissue of a subject; a plunger configured to simultaneously depress within the first chamber and the second chamber; and a needle in fluid communication with the first chamber and the second chamber, wherein the first chamber and second chamber are configured to deliver through the needle an amount of the first polymer formulation, the substantially solvent-free first polymer formulation, or the first solvent-free polymer formulation and an amount the second polymer formulation, the substantially solvent-free second polymer formulation, or the second liquid solvent-free polymer formulation when the plunger is depressed.

The dual-chamber syringe is configured to mix the first polymer formulation, the substantially solvent-free first polymer formulation, or the first solvent-free polymer formulation and the second liquid solvent-free polymer formulation when the plunger is depressed. For example, the first polymer formulation, the substantially solvent-free first polymer formulation, or the first solvent-free polymer formulation and the second polymer formulation, the substantially solvent-free second polymer formulation, or the second liquid solvent-free polymer formulation can be mixed within tissue when administered to tissue. In another example, dual-chamber syringe can further comprise a mixer, such as a static mixer, where the first polymer formulation, the substantially solvent-free first polymer formulation, or the first solvent-free polymer formulation and the second polymer formulation, the substantially solvent-free second polymer formulation, or the second liquid solvent-free polymer formulation are mixed outside of tissue and the mixture of the first polymer formulation, the substantially solvent-free first polymer formulation, or the first solvent-free polymer formulation and the second polymer formulation, the substantially solvent-free second polymer formulation, or the second liquid solvent-free polymer formulation is subsequently injected into the tissue.

In one aspect, the dual-chamber syringe is configured to allow the first polymer formulation, the substantially solvent-free first polymer formulation, or the first solvent-free polymer formulation and the second polymer formulation, the substantially solvent-free second polymer formulation, or the second liquid solvent-free polymer formulation to be administered simultaneously. In another aspect, the dual-chamber syringe is configured to allow the first polymer formulation, the substantially solvent-free first polymer formulation, or the first solvent-free polymer formulation and the second polymer formulation, the substantially solvent-free second polymer formulation, or the second liquid solvent-free polymer formulation to be administered sequentially.

The amount of the first polymer formulation, the substantially solvent-free first polymer formulation, or the first solvent-free polymer formulation and the amount the second polymer formulation, the substantially solvent-free second polymer formulation, or the second liquid solvent-free polymer formulation can be controlled by the size of the first and second chamber. Also, the amounts of the first polymer formulation, the substantially solvent-free first polymer formulation, or the first solvent-free polymer formulation and the amount the second polymer formulation, the substantially solvent-free second polymer formulation, or the second liquid solvent-free polymer formulation can be varied relative to each other depending on the desired properties of the formed elastomer.

Also disclosed herein is a kit comprising a first container comprising a first compartment comprising a first polymer formulation, a substantially solvent-free first polymer formulation, or a first solvent-free polymer formulation capable of crosslinking and forming an elastomer when administered into a tissue or onto a surface of a tissue of a subject; and a sterile administration device.

In one aspect, the first container can be a syringe, bottle, or beaker. In one aspect, the first compartment can be a first chamber in a syringe. In another aspect, the bottle or beaker can contain the first compartment.

In one aspect, the sterile administration device is a needle, a spreader, such as a spatula, ladle, spoon, knife, or mixing rod.

In one aspect, the first container further comprises a second compartment comprising a second polymer formulation, a substantially solvent-free second polymer formulation, or a second liquid solvent-free polymer formulation capable of crosslinking with the first polymer formulation, the substantially solvent-free first polymer formulation, or the first solvent-free polymer formulation and forming an elastomer when administered into the tissue or onto the surface of the tissue of the subject. The first and second compartments are separated from each other such that the first polymer formulation, the substantially solvent-free first polymer formulation, or the first solvent-free polymer formulation and the second polymer formulation, the substantially solvent-free second polymer formulation, or the second liquid solvent-free polymer formulation do not inadvertently mix. For example, the second compartment can be a second chamber in a syringe. In another aspect, the bottle or beaker contains a wall that separates the first compartment from the second compartment.

In one aspect, the kit further comprises a second container comprising a third compartment comprising a second polymer formulation, a substantially solvent-free second polymer formulation, or a second liquid solvent-free polymer formulation capable of crosslinking with the first polymer formulation, the substantially solvent-free first polymer formulation, or the first solvent-free polymer formulation and forming an elastomer when administered into the tissue or onto the surface of the tissue of the subject. For example, the second container can be a second syringe, a second bottle, or a second beaker.

In one aspect, the first container and the sterile administration device are configured to cooperate to simultaneously administer the first polymer formulation, the substantially solvent-free first polymer formulation, or the first solvent-free polymer formulation and the second polymer formulation, the substantially solvent-free second polymer formulation, or the second liquid solvent-free polymer formulation into the tissue or onto the surface of the tissue of the subject. In another aspect, the first container, second container, and the sterile administration device are configured to cooperate to simultaneously administer the first polymer formulation, the substantially solvent-free first polymer formulation, or the first solvent-free polymer formulation and the second polymer formulation, the substantially solvent-free second polymer formulation, or the second liquid solvent-free polymer formulation into the tissue or onto the surface of the tissue of the subject.

The first polymer formulation, the substantially solvent-free first polymer formulation, or the first solvent-free polymer formulation can comprise a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly(propylene fumarate), a poly(glycerol sebacate), a poly(ethylene terephthalate), a polycarbonate, a polyamide, a polystyrene, or a poly(tetrafluoroethylene), or a combination, or copolymer thereof. For example, the first liquid solvent-free polymer formulation can comprise a polysiloxane or a polyolefin comprising polyisobutylene, polyisoprene, polybutadiene, or combination, or copolymer thereof.

In one aspect, the first polymer formulation, the substantially solvent-free first polymer formulation, or the first solvent-free polymer formulation can further comprise a biological agent.

It is also contemplated that a solvent, such as a biologically acceptable solvent, can be present in the formulations disclosed herein. It is understood that solvent and diluent can be used interchangeably herein. For example, the first polymer formulation can comprise a biologically acceptable solvent. In another example, the substantially solvent-free first polymer formulation can comprise a biologically acceptable solvent. In yet another example, the second polymer formulation can comprise a biologically acceptable solvent. In yet another example, the substantially solvent-free second polymer formulation can comprise a biologically acceptable solvent. The biologically acceptable solvent can be any suitable biologically acceptable solvent including, but not limited to water, N-Methyl-2-pyrrolidone propylene glycol, polyethylene glycol, ethanol, dimethyl sulfoxide, glycofurol, Solketal, glycerol formal, and acetone. For example, an amount of water can be present in the formulations disclosed herein. For example, the formulations disclosed herein can comprise up to 70 wt % of the biologically acceptable solvent, such as up to 60 wt % of the biologically acceptable solvent, up to 50 wt % of the biologically acceptable solvent, up to 40 wt % of the biologically acceptable solvent, up to 30 wt % of the biologically acceptable solvent, up to 20 wt % of the biologically acceptable solvent, up to 15 wt % of the biologically acceptable solvent, up to 10 wt % of the biologically acceptable solvent, or up to 5 wt % of the biologically acceptable solvent.

It is also contemplated that one or more additives can be present in the formulations disclosed herein. For example, the formulations disclosed herein can comprise up to 50 wt % of the one or more additives. In another example, the formulations disclosed herein can comprise up to 40 wt % of the one or more additives. In yet another example, the formulations disclosed herein can comprise up to 30 wt % of the one or more additives. In yet another example, the formulations disclosed herein can comprise up to 20 wt % of the one or more additives. In yet another example, the formulations disclosed herein can comprise up to 15 wt % of the one or more additives. In yet another example, the formulations disclosed herein can comprise up to 10 wt % of the one or more additives. In yet another example, the formulations disclosed herein can comprise up to 5 wt % of the one or more additives. In yet another example, the formulations disclosed herein can comprise up to 3 wt % of the one or more additives. In yet another example, the formulations disclosed herein can comprise up to 1 wt % of the one or more additives. It is also contemplated that the formulations disclosed herein do not contain one or more additives.

Suitable additives include, but are not limited to, a biologically active compound, a pharmaceutically active compound, a supplement, such as a vitamin, a salt, a cell, a virus, a microparticle, a nanoparticle, a crystallite, an oil, such as silicone oil, an oligomer, a polymer, such a polyethylene glycol (PEG), poly(D, L-lactic acid) (PLA) or poly(D, L-lactic-co-glycolic acid) (PLGA), cellulose, hypromellose, guar gum, a contrast agent, a nucleic acid, a tackifier, DNA, RNA, a protein, a peptide, a hormone, a hemostatic agent, a surfactant, a sugar, a starch, an anti-oxidant, and a cannabinoid. The one or more additives can be present in an amount to achieve a desired effect. For example, the one or more additives, such as a pharmaceutically active compound, can be present in a therapeutically effective amount, which refers to an amount that is sufficient to achieve the desired result (e.g., that will elicit a biological or medical response of a subject, such as a human or animal) or to have an effect on an undesired condition. For example, a “therapeutically effective amount” refers to an amount that is sufficient to achieve the desired therapeutic result or to have an effect on undesired symptoms, but is generally insufficient to cause adverse side effects. In another example, particles, such as a microparticle or a nanoparticle, for example silica, can be present in an amount to alter the mechanical properties of the articles formed from the formulations disclosed herein.

The second polymer formulation, the substantially solvent-free second polymer formulation, or the second liquid solvent-free polymer formulation can comprise a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly(propylene fumarate), a poly(glycerol sebacate), a poly(ethylene terephthalate), a polycarbonate, a polyamide, a polystyrene, or a poly(tetrafluoroethylene), or a combination, or copolymer thereof. For example, the second polymer formulation, the substantially solvent-free second polymer formulation, or the second liquid solvent-free polymer formulation can comprise a polysiloxane or a polyolefin comprising polyisobutylene, polyisoprene, polybutadiene, or combination, or copolymer thereof.

In one aspect, the elastomer is formed by crosslinking a first cross-link moiety on a polymer in the first polymer formulation, the substantially solvent-free first polymer formulation, or the first solvent-free polymer formulation with an identical first cross-link moiety on the polymer in the first polymer formulation, the substantially solvent-free first polymer formulation, or the first solvent-free polymer formulation, thereby forming the elastomer. In one aspect, the first cross-link moiety is an isocyanate, amine, aldehyde, dienes, dienophile, epoxide, cyanoacrylate, thiol, catechol, oligonucleotide, hydrogen bond donor/acceptor group, alkyne, azide, vinyl, acrylate, methacrylate, or hydroxyl group.

For example, the first cross-link moiety can be an isocyanate group, which can be cross-linked to amine group.

In one aspect, the elastomer is formed by crosslinking a second cross-link moiety on a polymer in the first polymer formulation, the substantially solvent-free first polymer formulation, or the first solvent-free polymer formulation with a third cross-link moiety on the polymer in the first polymer formulation, the substantially solvent-free first polymer formulation, or the first solvent-free polymer formulation, thereby forming the elastomer. In one aspect, each of the second cross-link moiety and the third cross-link moiety is hydrogen bond donor/acceptor groups, ureidopyrimidinone, maleimide, catechol, guaiacol, thiol, oligonucleotide, cyanoacrylate, amine, alkyne, azide, vinyl, acrylate, methacrylate, isocyanate, aldehyde, hydroxyl, epoxide, oxime, alkoxy, acetoxy, diene, or a dienophile group.

For example, the second cross-link moiety can be an amine group, and the third cross-link moiety can be an aldehyde group. In another example, the second cross-link moiety can be an amine group, and the third cross-link moiety can be an isocyanate group. In yet another example, the second cross-link moiety can be an azide group, and the third cross-link moiety can be an alkyne group. In yet another example, the second cross-link moiety can be a methacrylate group, and the third cross-link moiety can be a hydroxyl group. In yet another example, the second cross-link moiety can be a diene group, and the third cross-link moiety can be a dienophile group.

In one aspect, the elastomer is formed by crosslinking the first polymer formulation, the substantially solvent-free first polymer formulation, or the first solvent-free polymer formulation with a second polymer formulation, a substantially solvent-free second polymer formulation, or a second liquid solvent-free polymer formulation to form comprising a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly(propylene fumarate), a poly(glycerol sebacate), a poly(ethylene terephthalate), a polycarbonate, a polyamide, a polystyrene, or a poly(tetrafluoroethylene), or a combination, or copolymer thereof.

In one aspect, the elastomer is formed by crosslinking a fourth cross-link moiety on a polymer in the first polymer formulation, the substantially solvent-free first polymer formulation, or the first solvent-free polymer formulation with a fifth cross-link moiety on a polymer in the second polymer formulation, the substantially solvent-free second polymer formulation, or the second liquid solvent-free polymer formulation, thereby forming the elastomer. In one aspect, the fourth cross-link moiety and the fifth cross-link moiety is hydrogen bond donor/acceptor groups, ureidopyrimidinone, maleimide, catechol; thiol, oligonucleotide, cyanoacrylate, amine, alkyne, azide, vinyl, alkoxy, acrylate, methacrylate, isocyanate, aldehyde, hydroxyl, epoxide, diene, or a dienophile group.

For example, the fourth cross-link moiety can be an amine group, and the fifth cross-link moiety can be an aldehyde group. In another example, the fourth cross-link moiety can be an amine or hydroxyl group, and the fifth cross-link moiety can be an isocyanate group. In yet another example, the fourth cross-link moiety can be an azide group, and the fifth cross-link moiety can be an alkyne group. In yet another example, the fourth cross-link moiety can be a methacrylate group, and the fifth cross-link moiety can be a hydroxyl group. In yet another example, the fourth cross-link moiety can be a diene group, and the fifth cross-link moiety can be a dienophile group.

In one aspect, the first liquid polymer formulation, the substantially solvent-free first liquid polymer formulation, or the first liquid solvent-free polymer formulation comprises a polymer having a brush-like structure.

In one aspect, the second polymer formulation, the substantially solvent-free second polymer formulation, or the second liquid solvent-free polymer formulation comprises a polymer having a brush-like structure.

In a further aspect, the elastomer has an elastic modulus from about $10^2$ Pa to about $10^6$ Pa. In a still further aspect, the elastomer has an elastic modulus from about $10^2$ Pa to about $10^4$ Pa. In a still further aspect, the elastomer has an elastic modulus from about $10^4$ Pa to about $10^6$ Pa. In a still further aspect, the elastomer has an elastic modulus from about $10^3$ Pa to about $10^5$ Pa.

In a further aspect, the elastomer has an elastic modulus from about $10^2$ Pa to about $10^6$ Pa at a temperature of greater than about 90° F. In a still further aspect, the elastomer has an elastic modulus from about $10^2$ Pa to about $10^4$ Pa at a temperature of greater than about 90° F. In a still further aspect, the elastomer has an elastic modulus from about $10^4$ Pa to about $10^6$ Pa at a temperature of greater than about 90° F. In a still further aspect, the elastomer has an elastic modulus from about $10^3$ Pa to about $10^5$ Pa at a temperature of greater than about 90° F. For example, the temperature can be from about 90° F. to about 110° F., such as from about 90° F. to about 100° F.

In a further aspect, the elastomer has a strain-stiffening parameter of from about 0.1 to about 1. In a still further aspect, the elastomer has a strain-stiffening parameter of from about 0.1 to about 0.9, of from about 0.1 to about 0.8, of from about 0.1 to about 0.7, of from about 0.1 to about 0.6, of from about 0.1 to about 0.5, of from about 0.1 to about 0.4, of from about 0.1 to about 0.3, of from about 0.1 to about 0.2, of from about 0.2 to about 1, of from about 0.3 to about 1, of from about 0.4 to about 1, of from about 0.5 to about 1, of from about 0.6 to about 1, of from about 0.7 to about 1, of from about 0.8 to about 1, of from about 0.9 to about 1, of from about 0.2 to about 0.9, of from about 0.3 to about 0.8, or of from about 0.4 to about 0.7.

In a further aspect, the elastomer can undergo uniaxial elongation from about 2-fold to about 10-fold. In a still further aspect, the elastomer can undergo uniaxial elongation from about 2-fold to about 9-fold, from about 2-fold to about 8-fold, from about 2-fold to about 7-fold, from about 2-fold to about 6-fold, from about 2-fold to about 5-fold, from about 2-fold to about 4-fold, from about 2-fold to about 3-fold, from about 3-fold to about 9-fold, from about 4-fold to about 9-fold, from about 5-fold to about 9-fold, from about 6-fold to about 7-fold, from about 8-fold to about 9-fold, from about 3-fold to about 8-fold, or from about 4-fold to about 7-fold.

D. METHODS

Also disclosed herein is a method of administering the polymer formulations disclosed herein, such as the solvent-free polymer formulations disclosed herein into a tissue or onto a surface of a tissue of a subject to form an elastomer described herein in the tissue or on the surface of the tissue of the subject. As disclosed herein, the formed elastomer mimics the mechanical properties (softness and firmness) of biological tissues.

Disclosed herein is a method comprising the steps of administering a first liquid polymer formulation into a tissue or onto a surface of a tissue of a subject, and crosslinking the first liquid polymer formulation, thereby forming an elastomer inside the tissue or onto the surface of the tissue of the subject.

Disclosed herein is a method comprising the steps of administering a substantially solvent-free first liquid polymer formulation into a tissue or onto a surface of a tissue of a subject, and crosslinking the substantially solvent-free first liquid polymer formulation, thereby forming an elastomer inside the tissue or onto the surface of the tissue of the subject.

Disclosed herein is a method comprising the steps of administering a first liquid polymer formulation, a substantially solvent-free first liquid polymer formulation, or a first liquid solvent-free polymer formulation into a tissue or onto a surface of a tissue of a subject, and crosslinking the first liquid polymer formulation, the substantially solvent-free first liquid polymer formulation, or the first liquid solvent-free polymer formulation, thereby forming an elastomer inside the tissue or onto the surface of the tissue of the subject.

In one aspect, the subject can be a human or an animal, such as a dog or cat. For example, the subject can be a human.

In one aspect, the method further comprises the step of administering a second polymer formulation, a substantially solvent-free second polymer formulation, or a second liquid solvent-free polymer formulation into the tissue or onto the surface of the tissue of the subject, and wherein step b) comprises crosslinking the first liquid polymer formulation, the substantially solvent-free first liquid polymer formulation, or the first liquid solvent-free polymer formulation with the second polymer formulation, the substantially solvent-free second polymer formulation, or the second liquid solvent-free polymer formulation, thereby forming an elastomer inside the tissue or onto the surface of the tissue of the subject. For example, the administering of the first liquid polymer formulation, the substantially solvent-free first liquid polymer formulation, or the first liquid solvent-free polymer formulation and the second polymer formulation, the substantially solvent-free second polymer formulation, or the second liquid solvent-free polymer formulation can be performed simultaneously. In another example, the administering of the first liquid polymer formulation, the substantially solvent-free first liquid polymer formulation, or the first liquid solvent-free polymer formulation and the second polymer formulation, the substantially solvent-free second polymer formulation, or the second liquid solvent-free polymer formulation can be performed sequentially.

In one aspect, step b) comprises crosslinking a first cross-link moiety on a polymer in the first liquid polymer formulation, the substantially solvent-free first liquid polymer formulation, or the first liquid solvent-free polymer formulation with an identical first cross-link moiety on the polymer in the first liquid polymer formulation, the substantially solvent-free first liquid polymer formulation, or the first liquid solvent-free polymer formulation, thereby forming the elastomer inside the tissue or onto the surface of the tissue of the subject.

In one aspect, the formed elastomer is an implant, tissue adhesive, tissue repair, tissue fixation, tissue sealant, wound dressing, liquid bandage, tissue replacement, tissue regeneration (e.g., scaffolds for cell encapsulation), cells transplantation carriers (e.g., matrix, microgels), dermal filler, coating (e.g., coating of implantable medical devices, cell culture dishes), substrates for biological studies (e.g., mechanobiology), tissue augmentation, postsurgical adhesion prevention, or drug delivery system. For example, the formed elastomer can be an implant. In another example, the formed elastomer can be tissue replacement, such as the replacement of an intervertebral disc, adipose tissue, or breast tissue. For each application, the injectable formulation can be modified to possess desired functionality (e.g., chemical groups, ions, proteins, peptides) on polymer chains. For example, the injectable formulation can be modified to have functionalities that can be bound to desirable additives in the formed elastomer, such as pharmaceutically active compounds, particles, proteins, therapeutic compounds and the like. As such, the injectable formulation can serve as a platform for delivery of substances such as pharmaceutically active compounds to a subject.

In one aspect, the formed elastomer can be used for minimally invasive treatment of a range of complications including but not limited to vesicoureteric reflux, periprosthetical leakage of voice prostheses, faecal incontinence, laryngeal cleft, unilateral vocal fold paralysis, stomal leakage in continent diversion, and intervertebral disc.

In one aspect, the crosslinking can be reversible. As such, the elastomer can be manipulated post administration in the tissue or on the surface of the tissue to tune the mechanical properties of the elastomer. Thus, the method can further comprise the step of altering the degree of crosslinking in the elastomer. Reversible crosslinks allow for gel-to-sol transition through, for example, a minimally invasive stimuli-triggered (e.g. light, sound waves, enzyme) process. These degradable networks enable removal and manipulation of previously formed elastomers.

In one aspect, the crosslinking occurs over a period of time. The period of time can be from 1 second to 6 weeks. For example, the period of time can be from 1 second to 4 weeks, or from 1 second to 2 weeks, or from 1 min to 1 week, or from 1 min to 5 days, or from 1 min to 3 days, or from 1 min to 1 day, or from 1 min to 20 hours, or from 1 min to 16 hrs, or from 1 min to 12 hrs, or from 1 min to 8 hrs, or from 1 min to 6 hrs, or from 1 min to 4 hrs, or from 1 min to 2 hrs, or from 1 min to 1 hr, or from 30 min to 6 weeks, or from 1 hr to 6 weeks, or from 6 hr to 6 weeks, or from 12 hrs to 6 weeks, or from 1 day to 6 weeks, or from 3 days to 6 weeks, or from 5 days to 6 weeks, or from 1 week to 6 weeks.

In one aspect, the administering comprises injecting, casting, or molding. For example, the administering can comprise injecting. The injecting can be done with the dual chamber syringe disclosed herein. The injecting can also be done with the single barrel syringe disclosed herein. The injecting can be done using a needle to penetrate the skin and other tissue. The injecting can be done in a single injection or in multiple injections. In another example, the administering can comprise casting. In another example, the administering can comprise molding. The administering can be performed by components in the kits disclosed herein.

A non-limiting example of the formation of an implant by the method disclosed herein is show in FIGS. 3A-B. The disclosed implant with a brush like architecture can be altered to have mechanical properties of nearly soft biological tissue. There is no need for solvent to be present in the disclosed implant. Therefore, the implant does not leak, swell, or freeze, and remain invariantly functional over time in a broad range of environmental and physiological conditions.

E. ARTICLES

In one aspect, disclosed are articles formed from a disclosed elastomer. In a further aspect, the disclosure herein contemplates the use of the disclosed elastomers in the manufacture of certain items such as articles. Thus, in various aspects, a disclosed elastomer has been formed as an article such as, for example, implant, tissue adhesive, tissue repair, tissue fixation, tissue sealant, wound dressing, tissue replacement, dermal filler, coating, tissue augmentation, postsurgical adhesion prevention, or drug delivery system. For example, the article can be an implant, such as a breast implant. In another example, tissue replacement, such as the replacement of an intervertebral disc, adipose tissue, or breast tissue.

In one aspect, the article can be an artificial organ. The artificial organ can be produced by, for example, 3D printing.

In a further aspect, the elastomer has an elastic modulus from about $10^2$ Pa to about $10^6$ Pa. In a still further aspect, the elastomer has an elastic modulus from about $10^2$ Pa to about $10^4$ Pa. In a still further aspect, the elastomer has an elastic modulus from about $10^4$ Pa to about $10^6$ Pa. In a still further aspect, the elastomer has an elastic modulus from about $10^3$ Pa to about $10^5$ Pa.

In a further aspect, the articles disclosed herein can have an elastic modulus from about $10^2$ Pa to about $10^6$ Pa at a temperature of greater than about 90° F. In a still further aspect, the articles disclosed herein can have an elastic modulus from about $10^2$ Pa to about $10^4$ Pa at a temperature of greater than about 90° F. In a still further aspect, the articles disclosed herein can have an elastic modulus from about $10^4$ Pa to about $10^6$ Pa at a temperature of greater than about 90° F. In a still further aspect, the articles disclosed herein can have an elastic modulus from about $10^3$ Pa to about $10^5$ Pa at a temperature of greater than about 90° F. For example, the temperature can be from about 90° F. to about 110° F., such as from about 90° F. to about 100° F.

In another aspect, the article does not leach. For example, the formed article can leach less than 2%, less than 1%, less than 0.5%, or less than 0.25%.

F. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Experimental I—Rheological Measurements

Bottlebrushes with end-functionalized side chains are synthesized by atom transfer radical copolymerization of polydimethylsiloxane-methacrylate (PDMSMA) macromonomers and controlled fractions of polyethyleneglycol-methacrylate (PEGMA) macromonomers with either hydroxyl (OH—) or azide ($N_3$—) functionalized chain ends (see Synthesis Section). Bottlebrush synthesis was validated by molecular visualization of well-defined worm-like macromolecules (FIGS. 20A-C).

Figure 8:
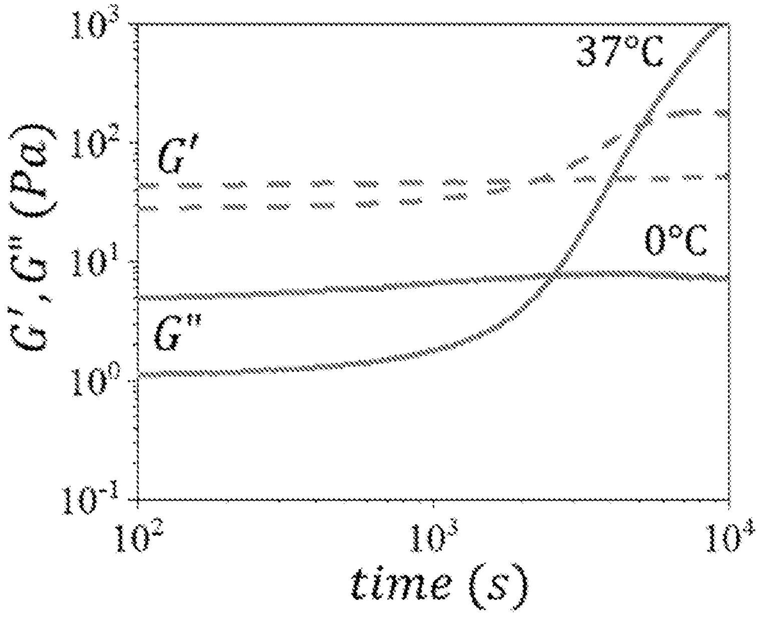
FIG. 8 shows evolution of elastic (G') and loss modulus (G") as a function of time for injectable elastomers composed of brush chains with hydroxyl groups cured with a macromolecular diisocyanate crosslinker NCO:OH (1:1) at temperatures of 0 and 37° C. The premixed injectable formulation shows gelation at elevated temperature (37° C.), while it remains flowable at low temperature (0° C.). The formulation remained flowable after 2 months storage at −20° C., and showed gelation with increasing temperature.

Upon injecting with a single barrel syringe (FIG. 3), a pre-mixed formulation of brush-like macromolecules with hydroxyl functionalized side chain ends and a macromolecular diisocyanate crosslinker NCO:OH(1:1) cures to yield solvent-free elastomers with tissue-mimetic properties (FIGS. 32A-B). The premixed injectable formulation shows gelation at elevated temperature (37° C.), while it remains flowable at low temperature (0° C.) (FIG. 8). The formulation remains flowable after 2 months storage at −20° C., and undergoes gelation with increasing temperature.

Injectable elastomers as tissue-mimetic implants are achieved by co-injection of two reactive components: (i) a melt of bottlebrushes with functionalized side chains, and (ii) a difunctional crosslinker (FIGS. 4A-D). Given the large size of bottlebrush macromolecules, a minuscule fraction of crosslinking moieties is required to achieve a fully conjugated network without polymerization-caused shrinkage.

Figures 9A, 9B:
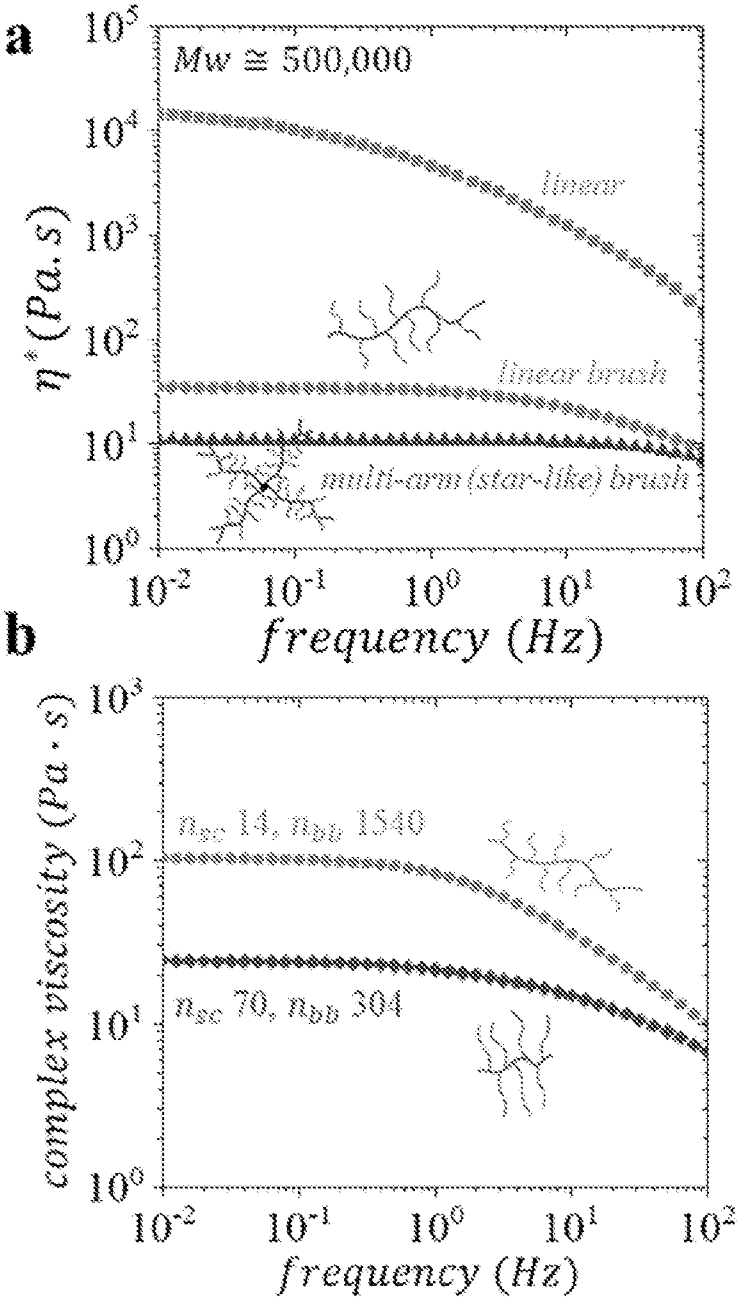
FIGS. 9A-B shows (9*a*) polydimethylsiloxane (PDMS) bottlebrush melts with varying architecture (e.g., linear brush, multi-arm (star-like) brush) demonstrate significantly (three orders of magnitude) lower viscosity compared to linear PDMS melt of similar molecular weight ($M_w$≅500,000). 9*b* shows PDMS bottlebrush melt with longer side chains, yet similar molecular weight ($n_{sc}$=14, $n_{bb}$=1540 vs. $n_{sc}$=70, $n_{bb}$=304) possess lower melt viscosity.

Solvent-free injection of brush melts is empowered by a significant reduction in viscosity relative to linear polymers of the same molecular weight due to limited overlap and entanglement of bottlebrush macromolecules (FIGS. 9A-B). Additional decrease of viscosity can be achieved by using star-like bottlebrush melts.

Figures 10A, 10B:
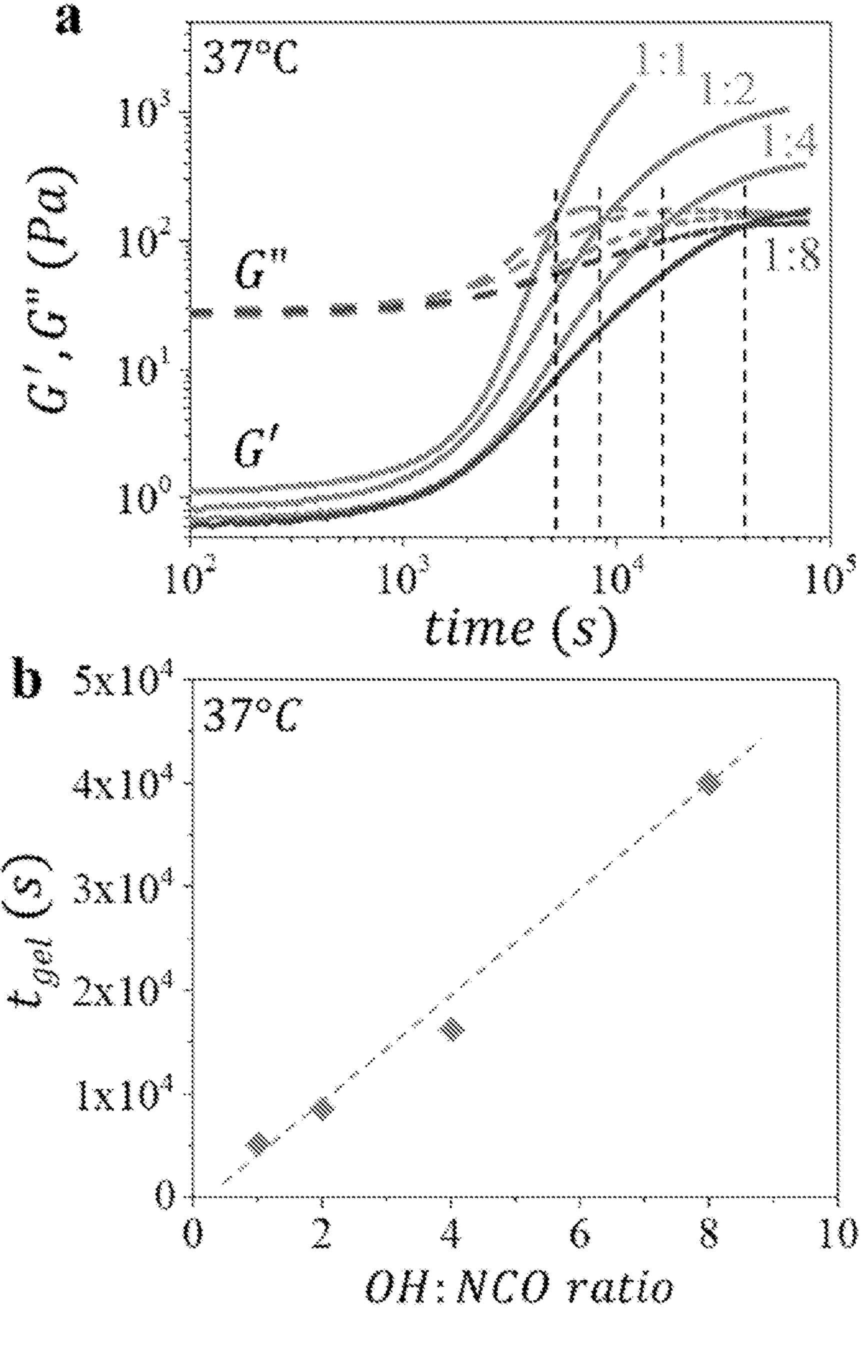
FIGS. 10A-B shows (10*a*) evolution of G' and G" as a function of time for injectable elastomers comprising decreasing NCO:OH ratios (1:1, 2, 4, or 8). 10b shows correlation of gelation time ($t_{gel}$) and ratio of NCO:OH functional groups.
Figures 11A, 11B:
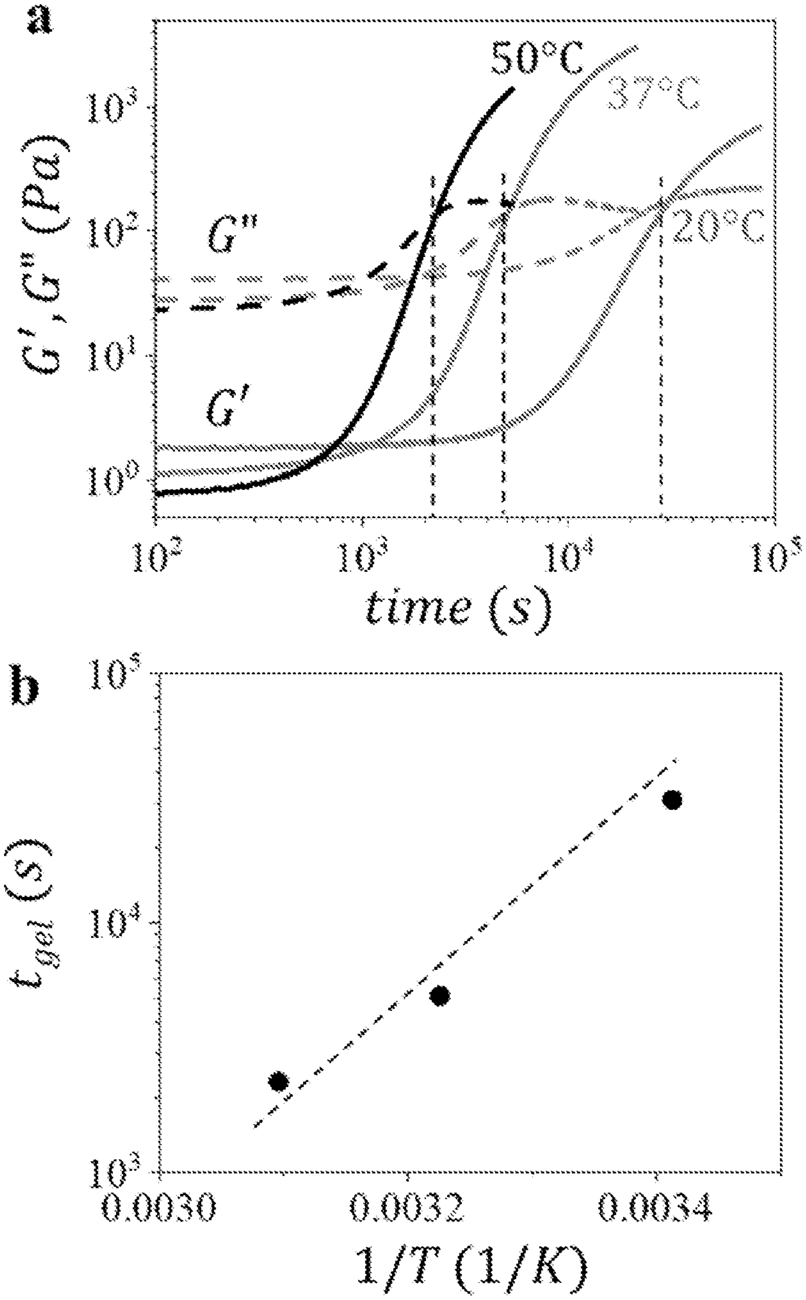
FIG. 11 shows (11*a*) evolution of G' and loss G" moduli as a function of time for injectable elastomers comprising NCO:OH (1:1) at increasing temperatures of 20, 37, and 50° C. 11*b* shows correlation of gelation time ($t_{gel}$) and temperature for injectable elastomers comprising NCO:OH (1:1).
Figures 12A, 12B:
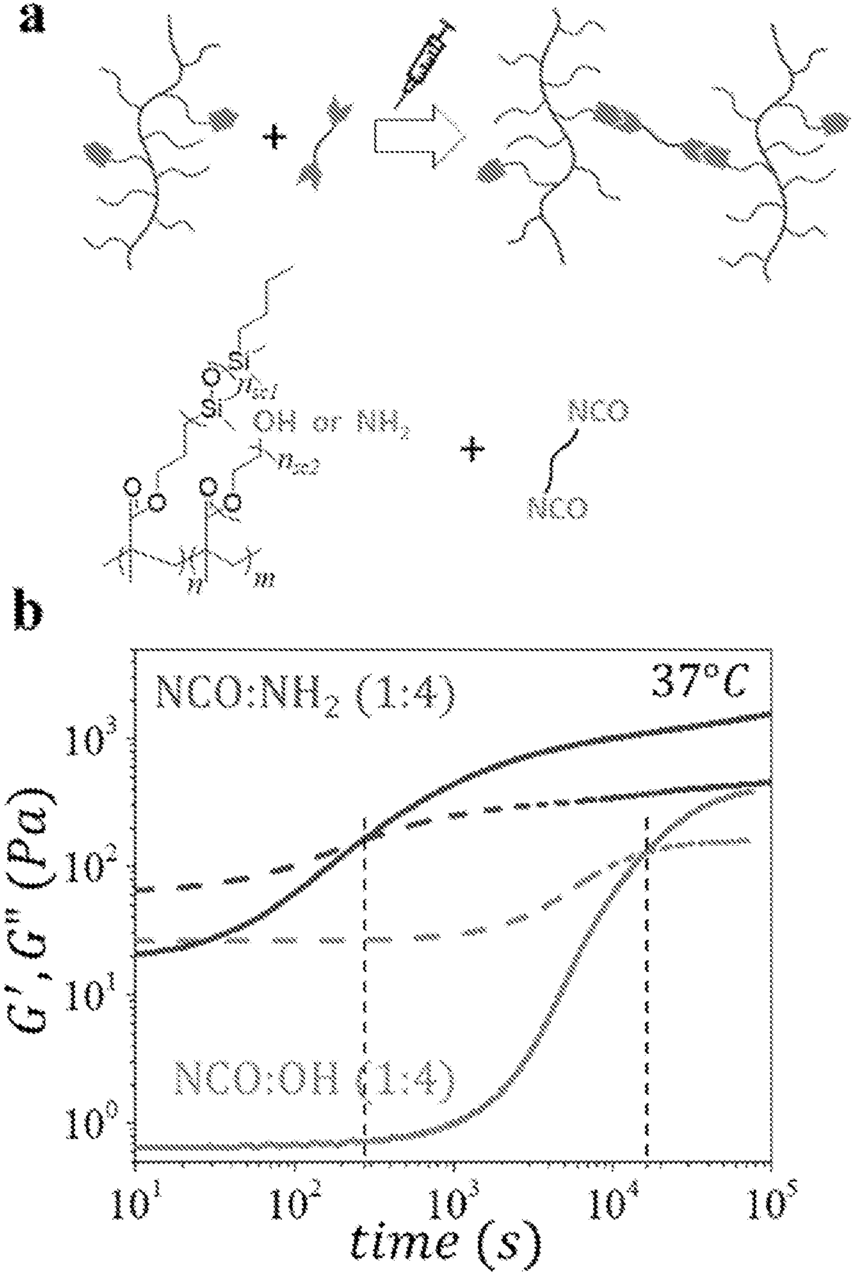
FIGS. 12A-B shows (12*a*) injectable tissue-mimetic elastomers composed of random polydimethylsiloxane-poly (ethylene glycol) (PDMS-r-PEG) brush polymers with a controlled fraction of end-functionalized side-chains and a linear difunctional crosslinker. 12*b* shows evolution of the storage (G') and loss (G") moduli as a function of time for injectable elastomers with either OH-functionalized or $NH_2$-functionalized brush chain ends cured with a macromolecular diisocyanate crosslinker.
Figure 13:
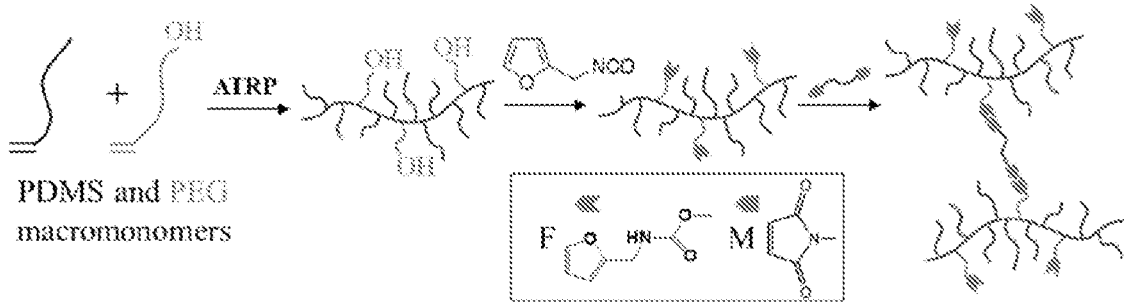
FIG. 13 shows synthesis of injectable super-soft solvent-free dual-component slow-cure self-healable (dynamic) elastomers based on Diels-Alder chemistry. Bottlebrush polymer parts were synthesized by controlled radical polymerization of polydimethylsiloxane methacrylate (PDMS) and polyethylene glycol methacrylate (PEG) macromonomers and converting of hydroxyl groups of polymer chains to Furan (F) moieties by reaction of hydroxyl groups with furfuryl isocyanate and crosslinker was synthesized by converting of hydroxyl groups of linear bi functional PDMS to maleimide (M).
Figures 14A, 14B:
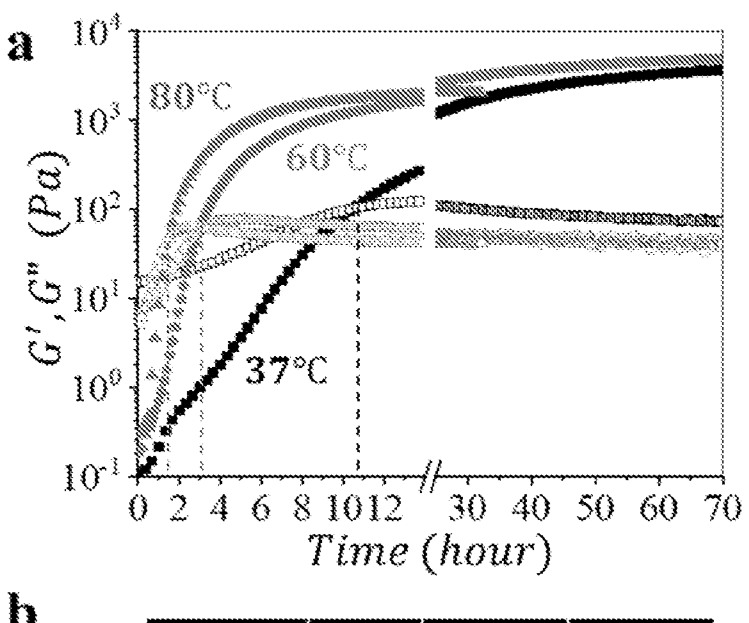
FIGS. 14A-B shows (14*a*) gelation of a formulation (Mixture of PDMS bottlebrush comprising 5 mol % of furan-functionalized PEG side chains and linear PDMS with maleimide moieties in both ends that the Furan/Maleimide mole ratio is one: F1M1 (14b) was monitored by measuring storage (G') and loss (G") moduli (1 rad/s, 5% strain) at three different temperatures as indicated (37, 60, and 80° C.). (b) Gelation ($\tau_g$) and equilibration times ($\tau_e$) for different temperatures.

Within a given crosslinking scheme (i.e. NCO:OH), a combination of stoichiometry and temperature allows tuning gelation time ($t_{gel}$) within more than two orders of magnitude as demonstrated by increasing $t_{gel}$ by either decreasing crosslinker concentration (FIGS. 10A-B) or temperature (FIGS. 11A-B). Similarly, switching from OH to $NH_2$ functionalization decreases $t_{gel}$ from hours to the minutes (FIG. 12), which can be exploited in future mixed OH/$NH_2$ functionalized brushes. Overall, the injectable technology contains a toolbox of architectural and chemical parameters to enable broad tuning of cure time to cover a significant portion of biomedical applications. It is important to note that tuning crosslinker concentration inadvertently augments both the curing time and mechanical properties. Therefore, to decouple $t_{gel}$ and $E_0$, we design bottlebrushes stoichiometrically enriched with OH-functionalized side chains relative to the crosslinker to adjust the gelation kinetics. These decoupling efforts can be explored through additional crosslinking chemistries (FIG. 2A-2J) such as reversible Diels-Alder reactions (FIGS. 13, 14A-B).

The wide range of curing time of injectable tissue-mimetic elastomers from seconds to weeks make them adjustable for various biomedical applications (e.g. from tissue-adaptive adhesives/sealants to minimally invasive revision plastic surgeries). The tunable gelation kinetics and tissue-like mechanics of the developed injectable elastomers enable them to be used as a whole or a part of a biomedical product. The formed elastomers may be loaded with bioactive agents to enable controlled delivery applications.

2. Experimental I—Biocompatibility Studies

Figure 15:
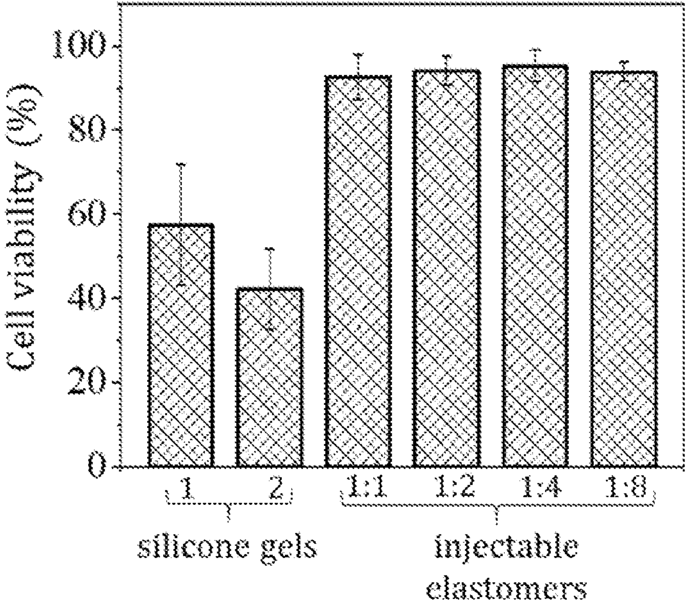
FIG. 15 shows comparing cytotoxicity of commercial silicone gels and injectable silicone brush elastomers (NCO:OH 1:1→1:8).

Cytotoxicity tests are performed according to ISO 10993-5 for the aqueous extractions with a NIH/3T3 fibroblast viability above 90% when exposed to injectable formulation extracts after 24 hours (FIG. 15), while extracts from commercial silicone gel implants show significantly diminished viability of 40-60%. The superior cell viability of injectable elastomers highlights their lack of acute cytotoxicity on isolated cells in vitro due to their leachable-free nature.

Figures 16A, 16B:
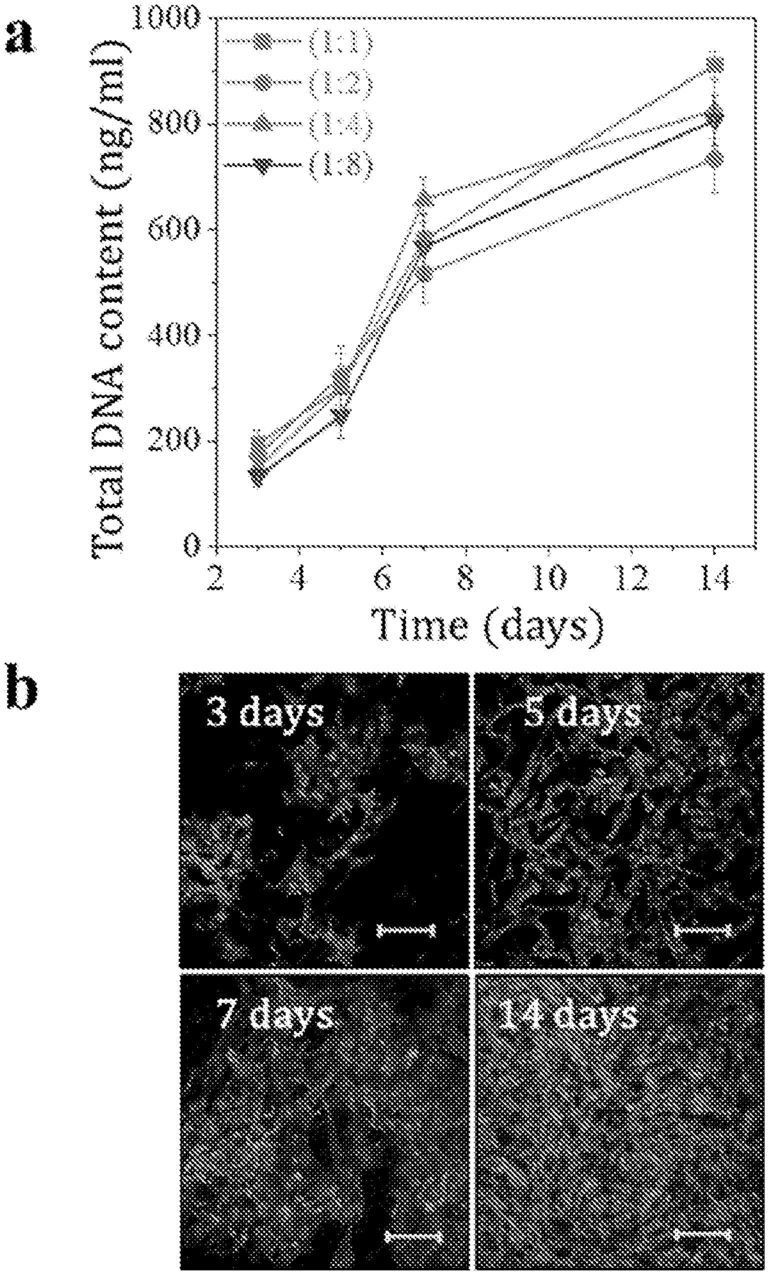
FIGS. 16A-B shows (16a) the extracted DNA quantification of cultured fibroblasts on injectable elastomers (NCO:OH 1:1→1:8) after 3, 5, 7, and 14 days. 16b shows proliferation of NIH/3T3 fibroblasts cultured to the injectable elastomer NCO:OH 1:8 monitored by fluorescence microscopy after 3, 5, 7, and 14 days (actin cytoskeleton and nucleus are displayed in green and blue, respectively).

The proliferation of NIH/3T3 fibroblasts is analyzed by measuring the total DNA content of cultured fibroblasts. The total extracted DNA from cultured cells on elastomer surfaces confirm increasing cell count over two weeks for each injectable formulation (FIG. 16A). This is visually confirmed by time-resolved fluorescence imaging (FIG. 16B), which affirms the injectable elastomer formulations as viable biocompatible materials.

Figures 17A, 17B:
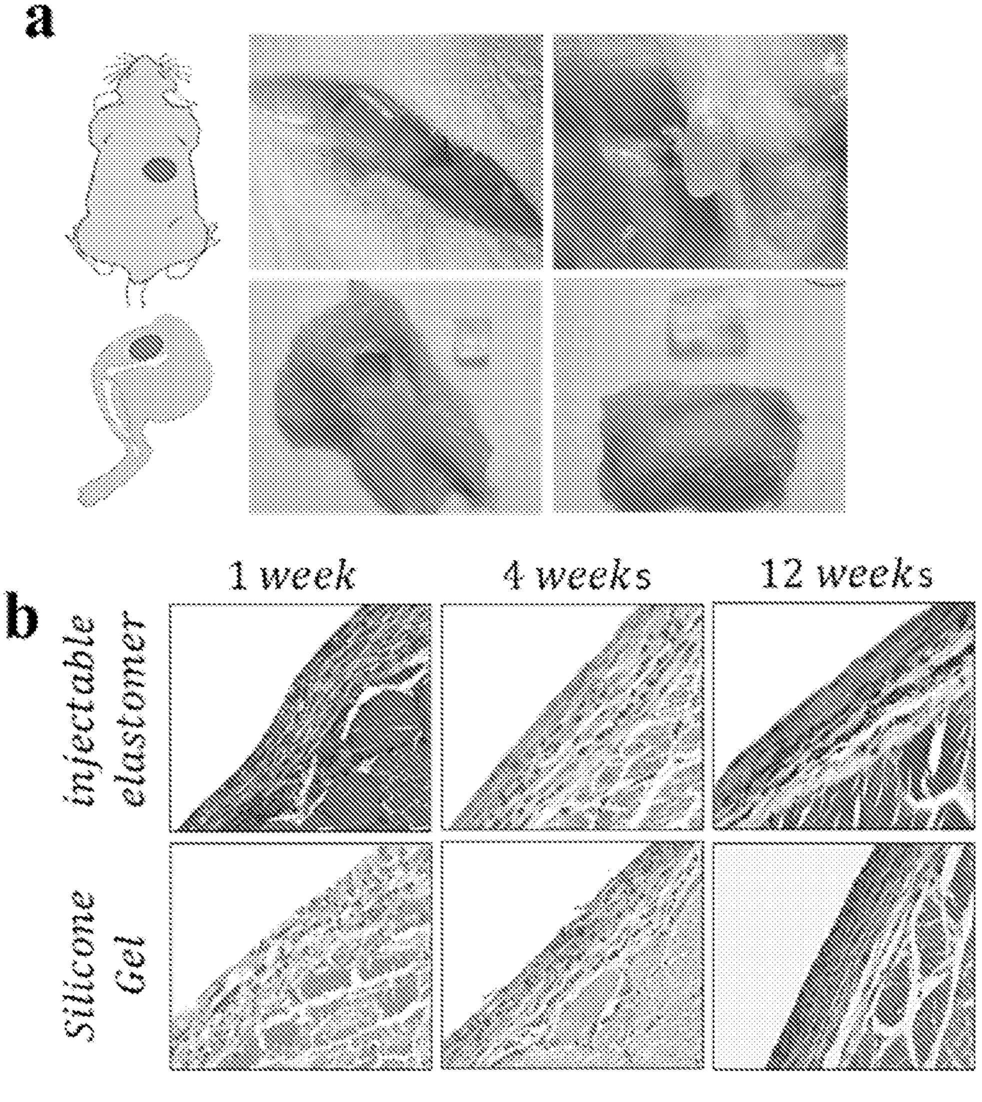
FIG. 17A-B shows (17a) schematic and explanted specimens of the injectable elastomer NCO:OH 1:8 (left panel), and a commercial silicone gel (right panel) after 12 weeks subcutaneous (top), and intramuscular (bottom) administration. 17b shows histology of intramuscular specimens at 1, 4, and 12 weeks explanation of the injectable elastomer NCO:OH 1:8 and a commercial silicone gel stained with hematoxylin and eosin.

In vivo assessment of injectable elastomers is conducted using animal models subjected to both subcutaneous and intramuscular implantation (FIG. 17A). In each case, explanted samples are well tolerated, with no clinical evidence of inflammatory response in surrounding tissues. In the subcutaneous explants, a thin translucent layer of encapsulating connective tissue is observed, which is significantly thicker around silicone gels. In muscle tissue, the injectable samples are fully intact and can be thoroughly explanted in contrast to the disfigured and partially fragmented silicone gels (FIG. 17A). According to the Hematoxylin-Eosin staining overview, the injectable elastomer capsule does not contain multinucleated foreign body giant cells at any stage and does not contain lymphocytes, leucocytes, macrophages on later stages, suggesting the implanted materials preclude chronic inflammation and are sufficiently inert (FIG. 17B).

Figures 18A, 18B:
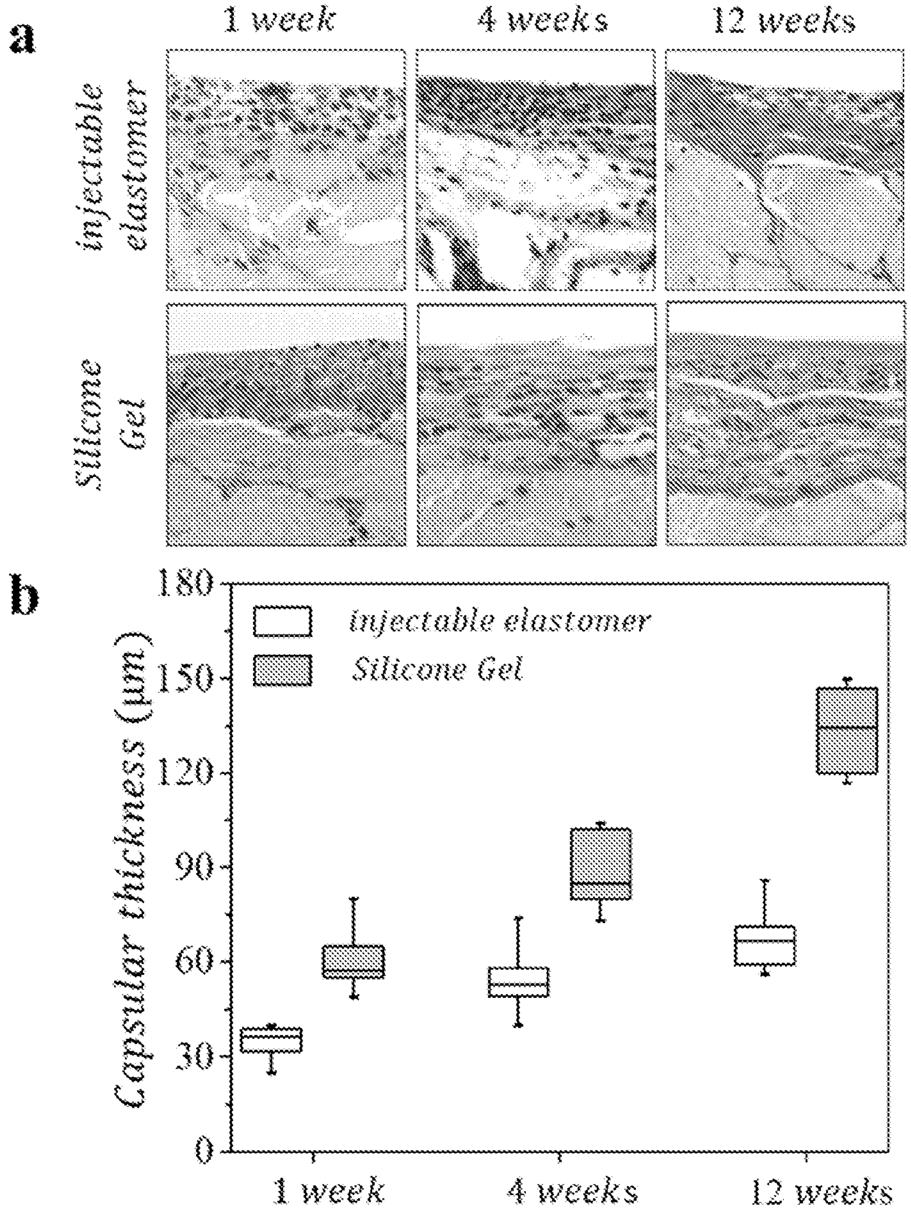
FIGS. 18A-B shows (18a) histology of intramuscular specimens at 1, 4, and 12 weeks explanation of the injectable elastomer NCO:OH 1:8 and a commercial silicone gel stained with the Mallory's procedure. 18b compares thickness of the fibrous layer in injectable elastomer NCO:OH 1:8 and Silicone Gel-1 explanted at 1, 4 and 12 weeks. The boxplot displays the distribution of the raw data.

The capsular thickness of the fibrous layer was quantified by morphometric image analysis on the Mallory's trichrome stained slides (FIG. 18A). The injectable elastomer samples display significantly lower capsular thickness compared to silicone gels at 1, 4 and 12 weeks (FIG. 18B), which may be ascribed to both the lack of leaching into the animal and their tissue-matching softness.

Figures 19A, 19B:
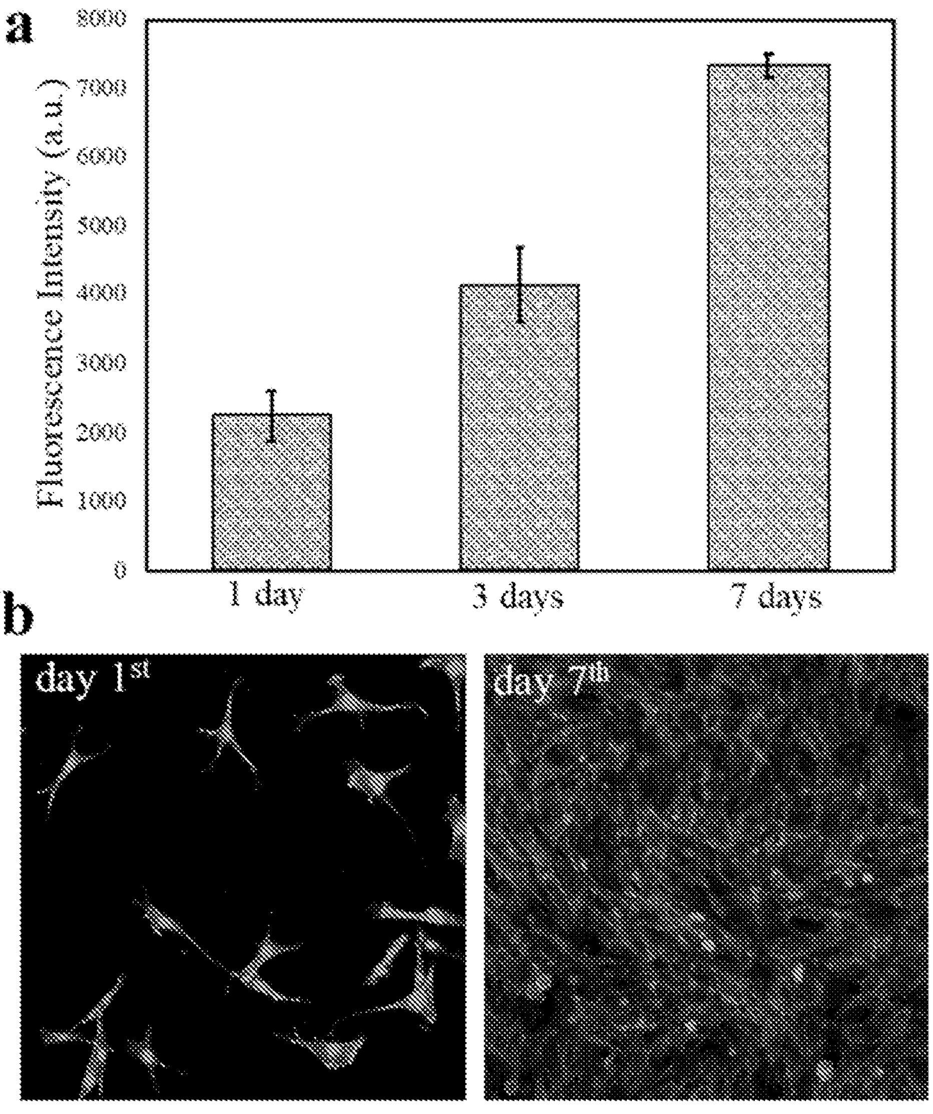
FIGS. 19A-B shows (19a) the extracted DNA quantification of cultured fibroblasts on injectable super-soft solvent-free dual-component slow-cure self-healable (dynamic) elastomer (F1M1) after 1, 3, and 7 days. 19b shows proliferation of fibroblasts cultured to the F1M1 injectable elastomer monitored by fluorescence microscopy after 1 and 7 days (actin cytoskeleton and nucleus are displayed in green and blue, respectively).
Figure 20:
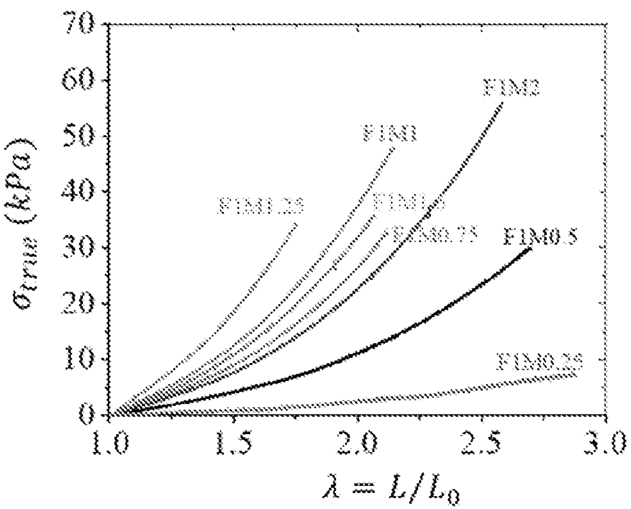
FIG. 20 shows mechanical properties of injectable supersoft solvent-free dual-component slow-cure self-healable (dynamic) elastomers based on Diels-Alder chemistry: True stress versus elongation-at-break for different fractions of furan (F) and maleimide (M) moieties, e.g., F1M1 corresponds to 1:1 molar ratio.

Super-soft solvent-free dual-component elastomers slowly-cured by Diels-Alder crosslinking reaction demonstrate proliferation of fibroblasts cultured on elastomer surface (FIGS. 19A-B). The mechanical properties of a solvent-free dual-component elastomers slowly-cured by Diels-Alder crosslinking reaction with different fractions of furan (F) and maleimide (M) moieties is shown in FIG. 20.

Figure 21:
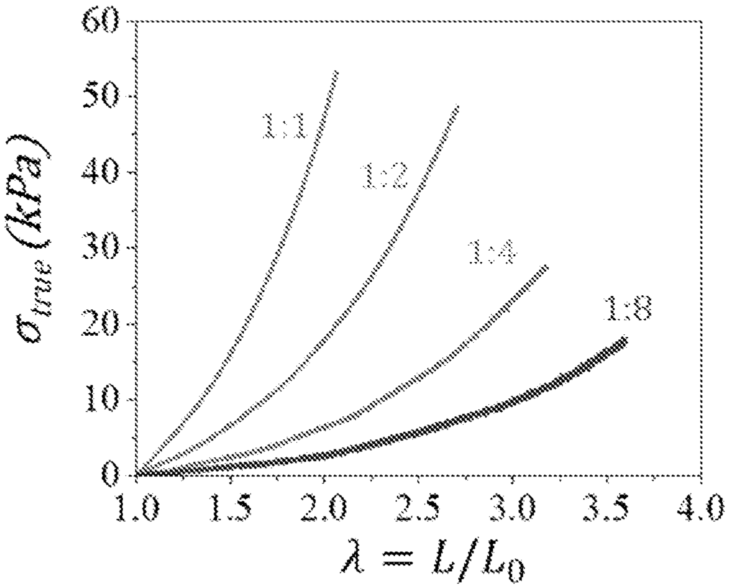
FIG. 21 shows replication of gels mechanics with solvent-free supersoft injectable elastomers. Injectable solvent-free supersoft and super-elastic implants replicating mechanics of soft biological tissues True stress-elongation ($\sigma_{true}$–λ) curve profiles of the injectable supersoft solvent-free elastomer series with decreasing NCO:OH molar ratios of (1:1→1:8), respectively show both decreasing softness ($E_0$) and firmness (β).
Figure 22:
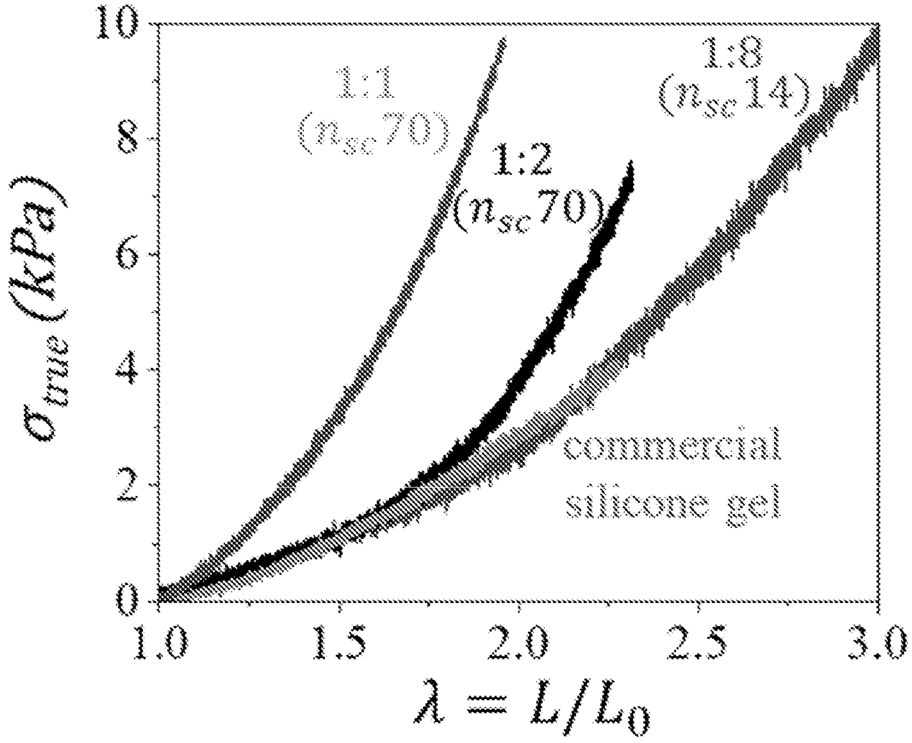
FIG. 22 True stress-elongation curve profiles of injectable elastomers with similar $E_0$ but different β in comparison with a commercial implant composed of silicone gel.

Mechanical behavior. The mechanical properties of brush-like elastomers are controlled by three architectural parameters [$n_x$, $n_{sc}$, $n_g$], which respectively correspond to the degree of polymerization (DP) of the bottlebrush backbone between two crosslinks, the side chains, or the backbone spacers between neighboring side chains. First, we explore $n_x$ by adjusting the NCO:OH molar ratio by varying crosslinker concentration at a constant molar fraction of OH-functionalized side chains (5 mol %). Similar to conventional linear chain polymer networks, increasing $n_x$ concurrently reduces the density of stress supporting strands and increases strand flexibility leading to enhanced softness at the expense of decreased firmness. This effect is clearly observed in FIG. 21 as decreasing the NCO:OH ratio (1:1→1:8) respectively results in lower Young's modulus ($E_0$) and less intense strain-stiffening, i.e. lower firmness (β). To increase firmness at a desired softness, we exploit the dual effect of longer side chains, which concurrently extend bottlebrush network strands and dilute the crosslinks. Respectively, bottlebrush elastomers with longer side chains ($n_{sc}$=70) demonstrate enhanced strain-stiffening while maintaining tissue-relevant softness (FIG. 22). Injectable elastomer [400,14] demonstrate nearly identical softness and firmness with a silicone gel (~30 wt % gel fraction) extracted from a commercial breast implant (FIG. 22), yet the solvent-free elastomers are more resilient and demonstrate significantly higher elastic deformation prior to fracture ($\lambda_{max}$).

Figure 23A:
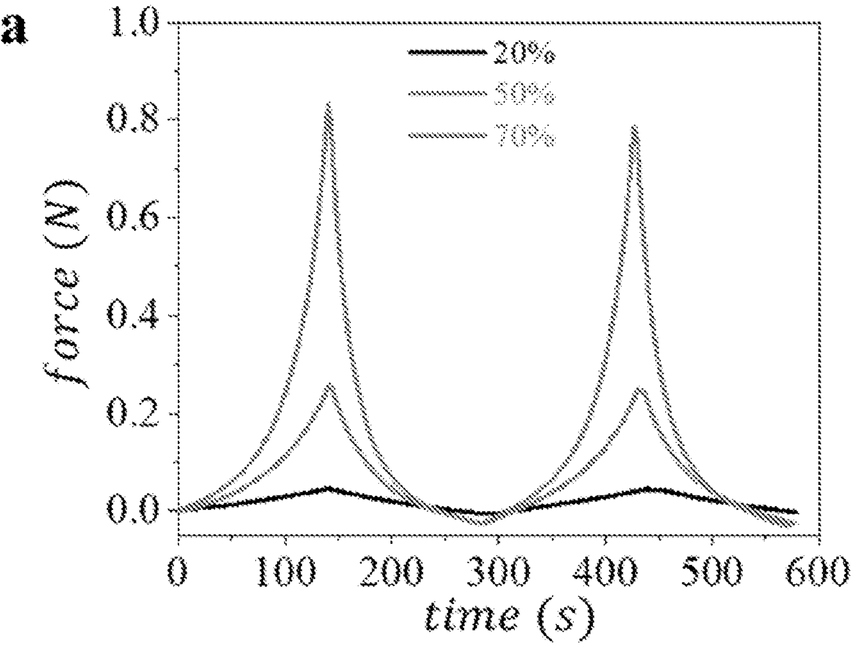
FIGS. 23A-B shows (23a) texture profile analysis (TPA) of the injectable elastomer for NCO:OH molar ratio of 1 to 8 at different strain ratios of 20, 50, and 70%, 23b shows comparison of the TPA parameters (springiness, resilience, and cohesiveness) of the injectable elastomer for NCO:OH molar ratio of 1 to 8 in comparison with a commercial implant composed of silicone gel at different strain ratios of 20, 50, and 70%.
Figure 23B:
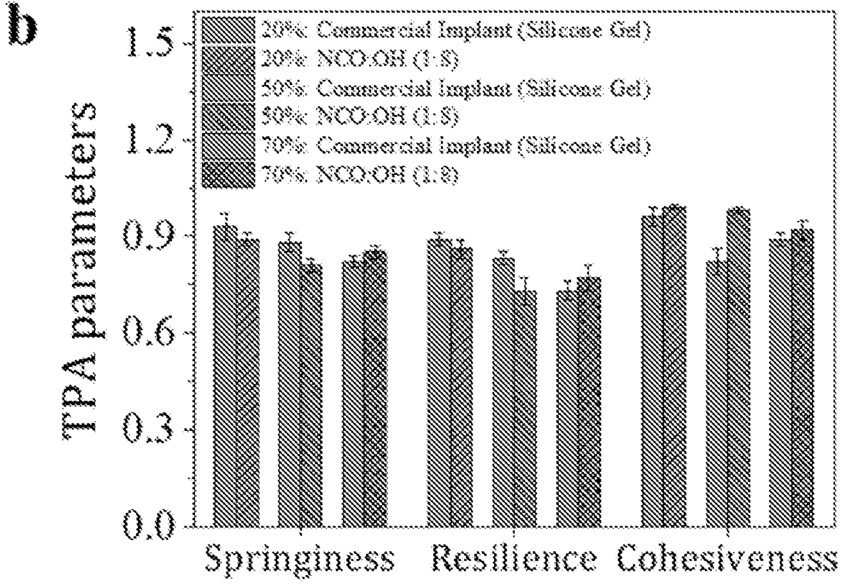
Figures 24A, 24B:
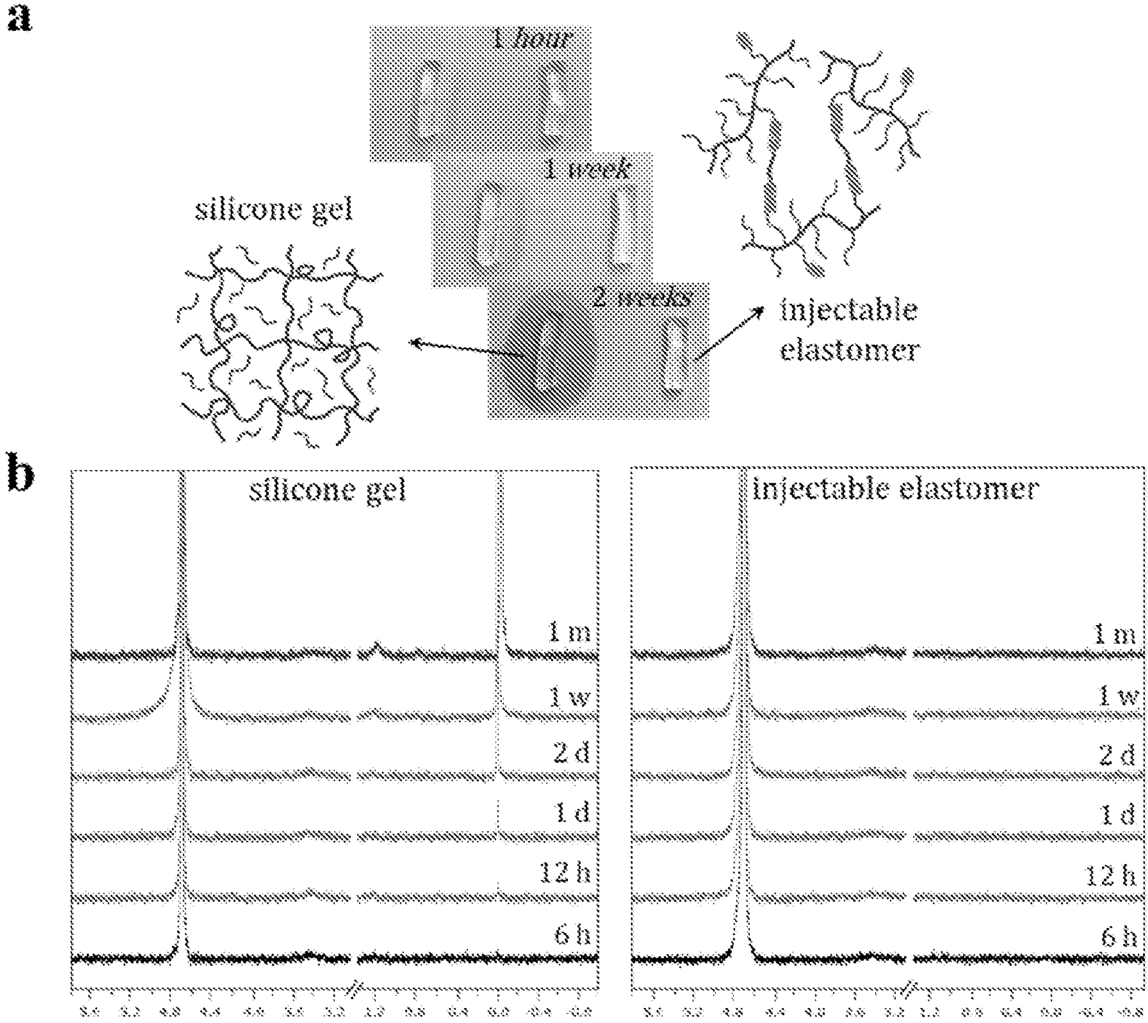
FIG. 24A-B shows (24a) a paper-based test reveals leaching from a commercial silicone gel used in breast implants versus the non-leaching injectable silicone brush elastomer (NCO:OH 1:8). 24b shows time-resolved $^1$H-NMR of sol extract from the commercial silicone gel and a NCO:OH (1:8) injectable elastomer in $D_2O$ monitored over one month (400 MHZ, $CDCl_3$): 4.70 (residual $H_2O$), 1.17, 0.01 (leachable materials).
Figure 25:
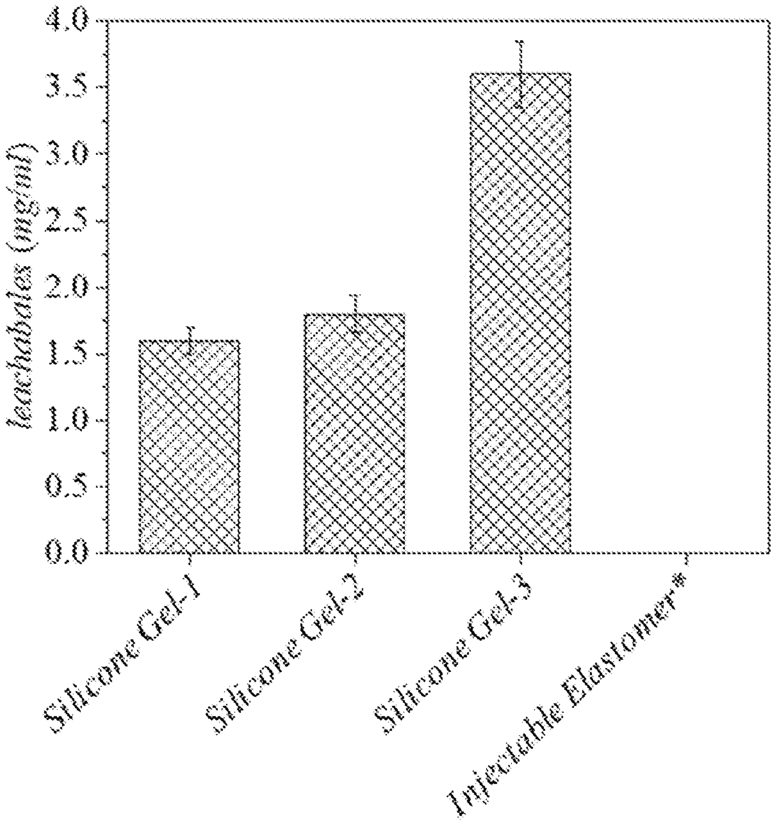
FIG. 25 shows leachability of three types of commercial silicone gel implants into aqueous medium over a month compared to the injectable elastomer* of NCO:OH (1:8) (400 MHz, $CDCl_3$); data shows mass of leachables from 5 gr gel after one month incubation in 10 ml aqueous medium at room temperature.

To further demonstrate the adequate mechanics of injectable elastomers, a texture profile analysis (TPA) was conducted, whereby cylindrical samples are subjected to cyclic compressions at different deformations (FIG. 23A). From the TPA profiles, several industrially relevant mechanical characteristics were evaluated such as springiness, resilience, and cohesiveness that favorably compare the solvent-free injectable elastomers with a commercial gel containing ~70% of liquid fraction (FIG. 23B). Furthermore, injectable elastomers does not leach, as compared to commercial silicone gels, which readily leach onto a paper towel, as shown in FIG. 24A. This is corroborated by aqueous extraction of each material's sol fraction in time-resolved $^1$H-NMR, as shown in FIG. 24B. Cytotoxicity tests were performed according to ISO 10993-5 for the aqueous extractions, as shown in FIG. 25, with a NIH/3T3 fibroblast viability above 90% when exposed to injectable formulation extracts after 24 hours, while extracts from commercial silicone gel implants show significantly diminished viability of 40-60%. The superior cell viability of injectable elastomers highlights their lack of acute cytotoxicity on isolated cells in vitro due to their leachable-free nature.

3. Synthesis Procedures: Synthesis of (Macro)Monomers, (Functional) Bottlebrush Polymers, Cross-Linkers, and Elastomers (1)

Synthetic procedures related the materials disclosed herein can found in Published International Application No. WO 2019/152537 and Published U.S. Application 2018/0201785, which are incorporated herein by reference, specifically for their disclosure of synthetic procedures related the materials disclosed herein.

Specific non-limiting (macro)monomers and linkers for the disclosed injectable and moldable tissue-mimetic elastomer formulations area provided below. It should be noticed that in all synthetic procedure, "brush" is interchangeable with "comb," which means spacing between neighboring side chains on the backbone.

Examples of the synthesis of macromonomers to form injectable and moldable tissue-like elastomers are described below. Described are: polyisobutylene as an example of polyolefin-based macromonomers, poly(n-butyl acrylate) as an example of polyacrylate macromonomers, polydimethylsiloxane as an example of polysiloxane macromonomers, and poly(ethylene glycol) as an example of water soluble systems. It should be noticed that the synthetic procedures are exemplary and readily expandable to all macromonomers disclosed herein to design elastomers with different structures mentioned in FIGS. 2A-2J. Further, in some aspects macromonomers possess brush-like chemical structure, which results in brush-on-brush or brush-on-comb injectable and moldable tissue-like elastomers, as shown in FIG. 34A and FIG. 34B. Brush-like networks are defined by three independent structural parameters—the degrees of polymerization of the side chains ($n_{sc}$), of the spacer between neighboring side chains ($n_g$), and of the strand backbone ($n_x$). The [$n_{sc}$, $n_g$, $n_x$] triplets can be varied within the [1-150, 1-100, 50-2000] range, respectively.

Synthesis of polyisobutylene macromonomer. Polyisobutylene (PIB) macromonomers with various molecular weight in the range of 100-10,000 Da were synthesized according to the following procedure (Scheme (a) below). n-hexane was added to a Schlenk flask, temperature decreased to 0° C., and then n-hexane was degassed by dry nitrogen bubbling. Borane tetrahydrofuran (THF) complex solution 1 M in THF were added to the degassed flask. Methyl-vinylidene polybutene (PIB) was dissolved in n-hexane, gently degassed by nitrogen bubbling for 30 min, then added dropwise to the borane solution over 30 minutes at 0° C. The resultant mixture was incubated at 0° C. for further 5 hours. Sodium hydroxide solution (0.5 M) was added drop-wise followed by 30% hydrogen peroxide solution and kept for 2 hrs. Afterwards, distilled water and n-hexane were added to the reaction mixture. The organic supernatant was separated and washed with distilled water, dried over anhydrous magnesium sulfate and filtered before removing all n-hexane in vacuum.

The resultant polyisobutylene hydroxyl was dissolved in dry THF and degassed by gentle nitrogen bubbling for 30 minutes, cooled to 0° C. before the addition of triethylamine and degassed for 10 min. Acryloyl chloride diluted with THF was degassed for 30 minutes before dropwise addition to the polyisobutylene hydroxyl solution at 0° C. The temperature of reaction was maintained at 0° C. for a further 4 hours before reaching room temperature while stirring overnight. Reaction mixture was diluted with n-hexane and extracted with distilled water and methanol. The organic layer was dried over magnesium sulfate and filtered before removing all n-hexane in vacuum.

It should be noticed that the above procedure for synthesis of polyisobutylene macromonomers is exemplary, and other procedures such as Ritter reaction on exo-olefin-terminated PIB (Scheme (b) below) according to the following procedure can be conducted. Exo-olefin PIB was dissolved in a selective solvent and acrylonitrile. At room temperature and under vigorous stirring, concentrated $H_2SO_4$ was added, and the reactor was sealed. The mixture was stirred for 12 hrs, then quenched by pouring the reaction mixture into ice/water slurry, and stirred for an additional hour. After concentrating the mixture under $N_2$ stream, the PIB was precipitated in methanol, and worked up.

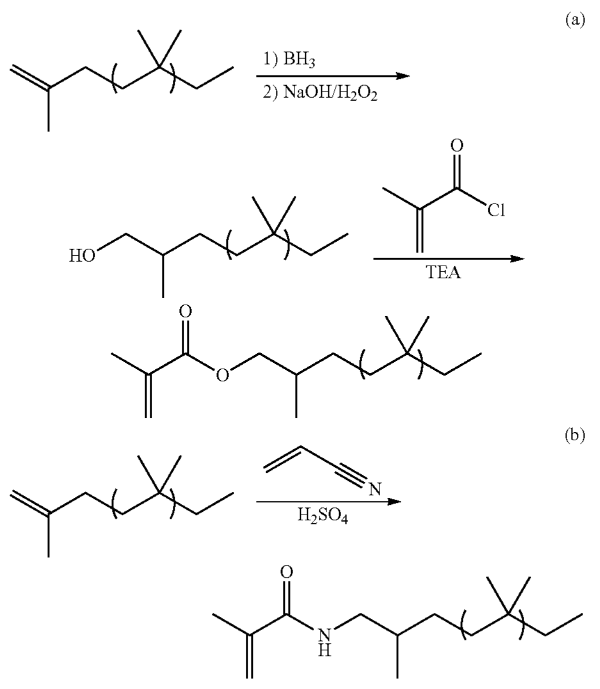

Synthesis of Polyisobutylene Macromonomer.

Synthesis of poly(n-butyl acrylate) macromonomer. Poly(n-butyl acrylate) (poly(n-BAx)) macromonomers with various degree of polymerization (x: 5-150) were synthesized as follows. Synthesis of poly(n-BA) macromonomers is as follows: A Schlenk flask equipped with a stir bar was charged with ethyl α-bromoisobutyrate (EBiB), nBA, N,N, N',N",N"-pentamethyldiethylenetriamine (PMDETA), and dimethylformamide (DMF). The solution was bubbled with dry nitrogen for 1 hr. Then, CuBr was added to the reaction mixture under nitrogen atmosphere. The flask was closed, purged for 5 min with nitrogen, and immersed in an oil bath thermostated at 65° C. The polymerization was stopped after 5 hrs when monomer conversion reached 80 mol % (determined using $^1$H NMR). The polymer solution was passed through a neutral aluminum oxide column and the unreacted monomers were evaporated by bubbling with nitrogen gas. The remaining polymer was dissolved in dimethyl acetamide (DMA) and transferred to a flask. Potassium acrylate was synthesized by reaction of acrylic acid (AA) and Potassium tert-butoxide (KOtBu) and added to the solution, which was stirred for 72 hrs at room temperature. The solution was filtered, diluted with methylene chloride (DCM), then washed with deionized (DI) water three times. The macromonomer solution was dried by adding magnesium sulfate ($MgSO_4$) and then by overnight evaporation in air.

Synthesis of functionalizable bottlebrush chains. Injectable and moldable tissue-mimetic elastomers (e.g., dual-component system), were made by synthesize bottlebrushes with a predetermined fraction of functionalizable end-groups on the side chains (0.1-100 mol. %) through controlled radical copolymerization of macromonomers. An example for injectable and moldable tissue-mimetic elastomers based on polysiloxane chemistry (e.g., poly(dimethylsiloxane)) is described herein. As an example, monomethacryloxypropyl-terminated poly(dimethylsiloxane) ($M_n$~1000 g/mol) and 0.3-5 mol. % of hydroxyl terminated poly(ethylene glycol) methacrylate ($M_n$~500 g/mol) were used as a co-macromonomer. The synthesis of functionalizable bottlebrush chains can readily be expandable to other macromonomers with different degree of polymerization (DP) in the range of 1-150, including but not limited to polyolefins like polyisobutylene, polyacrylates such as poly (n-BA), and poly(ethylene glycol) described above.

Synthesis of functionalizable multi-arm (star-like) bottlebrush macromolecules. Injectable and moldable tissue-mimetic elastomers (e.g., dual-component system), were made by synthesize bottlebrushes with a multi-functional (f>2) initiator to achieve predetermined fraction of functionalizable end-(terminal) hydroxyl groups on the backbone chains through controlled radical copolymerization of macromonomers. An example for injectable and moldable tissue-mimetic elastomers based on silicone chemistry (e.g., poly (dimethylsiloxane)) is described herein. As an example, monomethacryloxypropyl-terminated poly(dimethylsiloxane) ($M_n$~1,000 or 5000 or 10,000 g/mol) as macromonomer and allyl alcohol as chain termination agent were used. Fraction of hydroxyl terminated of star arms can be controlled from 0 to 100% to enable additional control of crosslink density and end-chain functionality. The synthesis of functionalizable bottlebrush star-like macromolecules can readily be expandable to other macromonomers with different degree of polymerization (DP) in the range of 1-150, including but not limited to polyolefins like polyisobutylene, polyacrylates such as poly(n-BA), and poly(ethylene glycol) mentioned above. The injectability and other rheological features (e.g., viscosity, shear-thinning) of the multi-arm (star-like) brush-like polymers are readily fine-tunable based on their macromolecular architecture to design injectable and moldable tissue-mimetic elastomers.

Figures 26A, 26B:
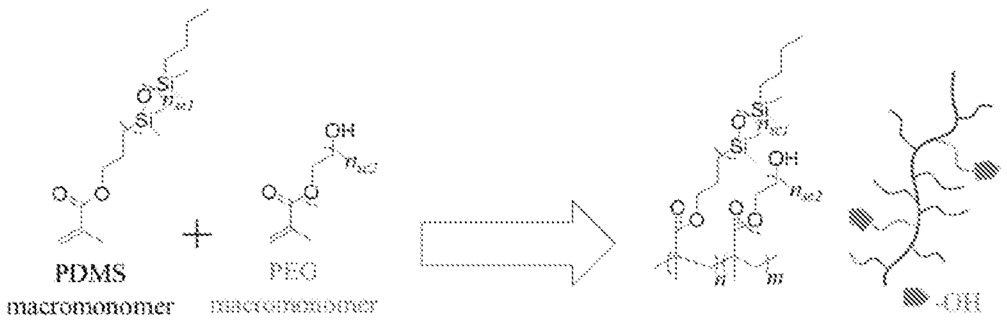
Figure 27:
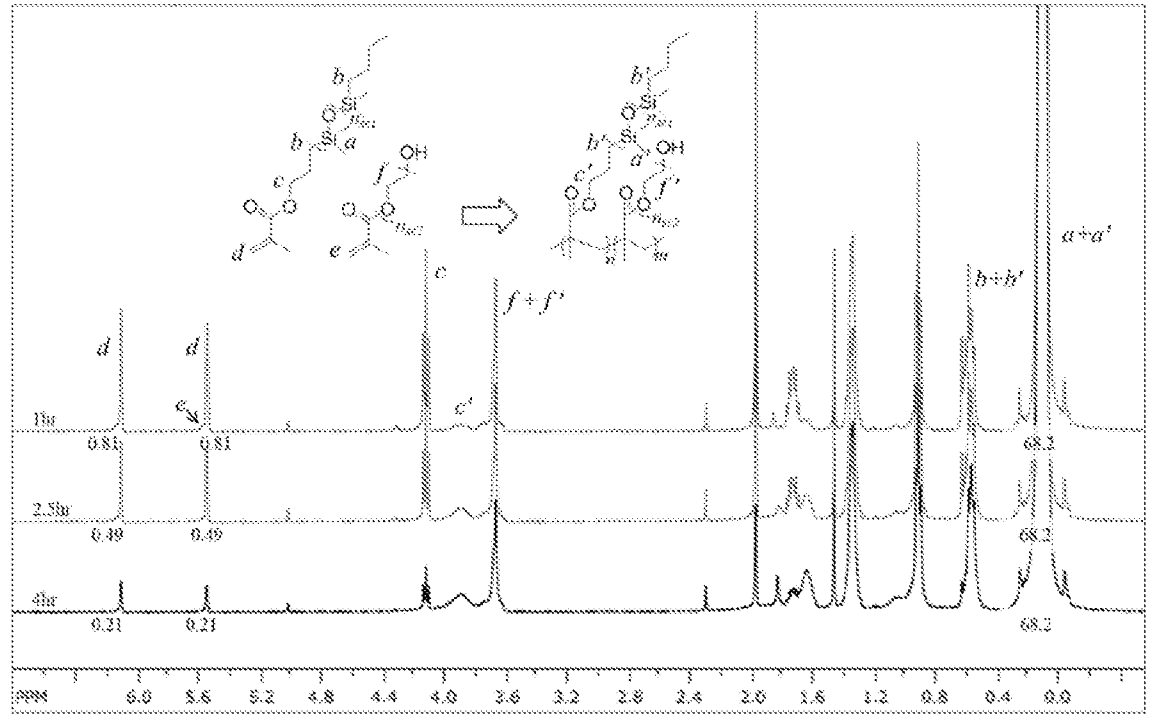
FIG. 27 Shows $^1$H-NMR growth of a random polydimethylsiloxane-poly(ethylene glycol) brush (PDMS-r-PEG, n:m, 95:5, $n_{sc1}$: 14, $n_{sc2}$: 12) (400 MHZ, $CDCl_3$): 6.16, 5.57 ($CH_2{=}C(CH_3)C{=}O$, PDMS and PEG macromonomer mixture, s, 1H), 4.12 (CO—$OCH_2$—, PDMS macromonomer, t, 2H), 3.91 (CO—$OCH_2$—, PDMS brush, t, 2H), 3.78 (CO—$OCH_2$—, PEG brush, t, 2H), 3.67 (—$OC_2H_4O$—, PEG brush, m, 32H), 0.55 (—$CH_2$—$(Si(CH_3)_2—O)_n$—$CH_2$—$CH_2$—, PDMS macromonomer and brush mixture, m, 4H), 0.09 (—$(Si(CH_3)_2—O)_n$—, PDMS macromonomer and brush mixture, s, 68.2H).

An exemplary procedure of controlled radical copolymerization in the case of polydimethylsiloxane (PDMS) is as follows: A 100 mL Schlenk flask equipped with a magnetic stir bar was charged with ethylene bis(2-bromoisobutyrate) (2-BiB), PDMS macromonomer, tris[2-(dimethylamino) ethyl]amine (Me6TREN), poly(ethylene glycol) methacrylate, and toluene. Prior to reaction, the solution was bubbled with dry nitrogen for 1.5 hr, then Cu(I)Cl was rapidly added to the reaction mixture under nitrogen atmosphere. The flask was sealed, purged for 15 minutes, and then immersed in a 45° C. oil bath. The polymerization was stopped after 12 hours to yield 80% macromonomers conversion as verified by $^1$H NMR, resulting in a polydimethylsiloxane-polyethylene glycol (PDMS-PEG·OH) bottlebrush polymer with DP of the backbone of interest. The polymer was purified to remove residual unreacted macromonomers. The resulting purified polymer was dried under vacuum at room temperature until a constant mass was reached. The reaction is exemplified in FIGS. 26A and 26B, and resulting NMR spectra are shown in FIGS. 27-29.

An exemplary procedure of controlled radical copolymerization poly(ethylene glycol) (PEG) is as follows: A 100 mL Schlenk flask equipped with a magnetic stir bar was charged with ethylene bis(2-bromoisobutyrate) (2-BiB), PEG macromonomer (poly(ethylene glycol) methyl ether methacrylate, average $M_n$ 500), tris[2-(dimethylamino)ethyl]amine (Me6TREN), poly(ethylene glycol) methacrylate (average $M_n$ 500), and toluene. Prior to reaction, the solution was bubbled with dry nitrogen for 1.5 hr, then Cu(I)Cl was rapidly added to the reaction mixture under nitrogen atmosphere. The flask was sealed, purged for 15 minutes. The polymerization was stopped after 12 hours to yield 80% macromonomers conversion as verified by $^1$H NMR, resulting in a poly(ethylene glycol) methyl ether-poly(ethylene glycol) (PEG-PEG.OH) bottlebrush polymer with DP of the backbone of interest. The polymer was purified to remove residual macromonomers. The resulting purified polymer was dried under vacuum at room temperature until a constant mass was reached.

Functionalization of bottlebrushes. In the next step, the hydroxyl groups on bottlebrushes are substituted with various functionalities (e.g., isocyanate or aldehyde/hydroxyl or amine, diene/dienophile, alkyne/azide). Isocyanate/Amine (FIG. 2 C, D). To substitute hydroxyl end groups with isocyanate moieties, OH-functionalized bottlebrushes were reacted with excess isophorone diisocyanate (IPDI) in the presence of dibutyltin dilaurate (DBTDL) as catalyst in anhydrous dichloromethane. Subsequently, the functionalized bottlebrushes were precipitated two times in anhydrous dimethylformamide to purify residual IPDI and DBTDL. The following procedure was performed to synthesize amine-terminated PEGMA macromonomer. A 100 ml round-bottom flask equipped with a magnetic stir bar was charged with 10 g PEGMA, 50 ml DCM, and 2.5 g triethylamine, sealed and then placed in an ice bath. Subsequently, 2.5 g methanesulfonyl chloride was added drop-wise to the mixture using a syringe pump, and reaction was stirred overnight. The resultant solution was passed through column for purification, and then dried. The obtained PEG derivate along with 50 ml DMF and 3 g sodium azide were charged into a 100 ml round-bottom flask equipped with a magnetic stir bar. The reaction was stirred for 24 h at room temperature. The mixture was centrifuged to remove excess salt, dried and then azide-terminated PEGMA macromonomer was extracted by dissolving in DCM followed by washing with water. The reactions are exemplified in FIG. 30. $^1$H-NMR spectrums of PEG macromonomer functionalization at different stages are shown in FIG. 31. A similar method as described above was followed to synthesize brush polymers using the PDMS macromonomer and azide-terminated PEGMA macromonomers. After purification of the brushes, they were dissolved in anhydrous THF, reacted with excess methanesulfonyl chloride, tris(hydroxypropyl)phosphine for 24 h, and then water was added to the mixture. Finally, the amine-functionalized brushes were purified via passing through column, and then dried for further use. $^1$H-NMR spectra of PDMS-r-PEG.$N_3$ and PDMS-r-PEG.$NH_2$ brush copolymers are displayed in FIG. 32. Finally, the dual-component fast-cure tissue-mimetic elastomers were prepared using injection and molding of the brush-like chains comprising isocyanate and amine functional groups through a dual-syringe system.

In order to synthesize single-component slow self-cure tissue-mimetic elastomers (FIG. 2B), hydroxyl groups on bottlebrushes were partially functionalized with isocyanate groups as described above. In this way, brush-like chains comprising desired ratio of isocyanate and hydroxyl functional groups on the same chain are synthesized.

The injectable elastomer formulations can comprise catalyst(s) including but not limited to amine and/or metallic salt catalysts such as tetramethyl butane diamine (TMBDA), 1-4 diazo (2,2,2) octane (DABCO), dibutyltin dilaurate (DBTDL), stannous octoate (SnOct), dimethylcyclohexylamine (DMCHA), dimethylethanolamine (DMEA), and bis-(2-dimethylaminoethyl) ether. The catalyst(s) content may vary in the range of 0-5000 ppm.

The linear and/or star-like brush-like polymers in the injectable formulations can be functionalized and/or cross-linked with (macro) molecules comprising two or more functional groups including but not limited to isocyanate, amine, aldehyde, dienes, dienophile, cyanoacrylate, thiol, catechol, oligonucleotide, hydrogen bond donor/acceptor group, ureidopyrimidinone, alkyne, azide, vinyl, acrylate, methacrylate, hydroxyl, maleimide, guaiacol, epoxide, oxime, alkoxy, or acetoxy group(s).

The linear and/or star-like brush-like polymers in the injectable formulations can be functionalized and/or cross-linked with (macro) molecules comprising two or more isocyanate groups including but not limited to toluene 2,4-diisocyanate (TDI), toluene 2,6-diisocyanate (TDI), 65:35 mixture of toluene 2,4 and 2,6-diisocyanate (TDI-65/35), 80:20 mixture of toluene 2,4 and 2,6-diisocyanate (TDI-80/20), 4,4'-diphenyl methane diisocyanate (MDI), 2,4'-diphenyl methane diisocyanate (MDI), 2,2'-diphenyl methane diisocyanate (MDI), hexamethylene diisocyanate (HDI), isophorone diisocyanate (IPDI), m-tetramethylxylene diisocyanate (m-TMXDI), dicyclohexylmethane 4,4'-diisocyanate (HMDI), triphenylmethane-4,4',4"-triisocyanate, naphthalene 1,5-diisocyanate (NDI), p-phenylene diisocynate (PPDI).

In specific embodiments the isocyanate groups on linear and/or star-like brush-like polymers in the injectable formulations can undergo reaction with ureas, urethanes, carboxylic acids, and self-addition reactions (i.e., react with themselves, forming dimers, trimers, polymers, carbodiimides and uretoneimines).

Figures 2A, 2B, 2C, 2D, 2E, 2F, 2G, 2H, 2I, 2J:
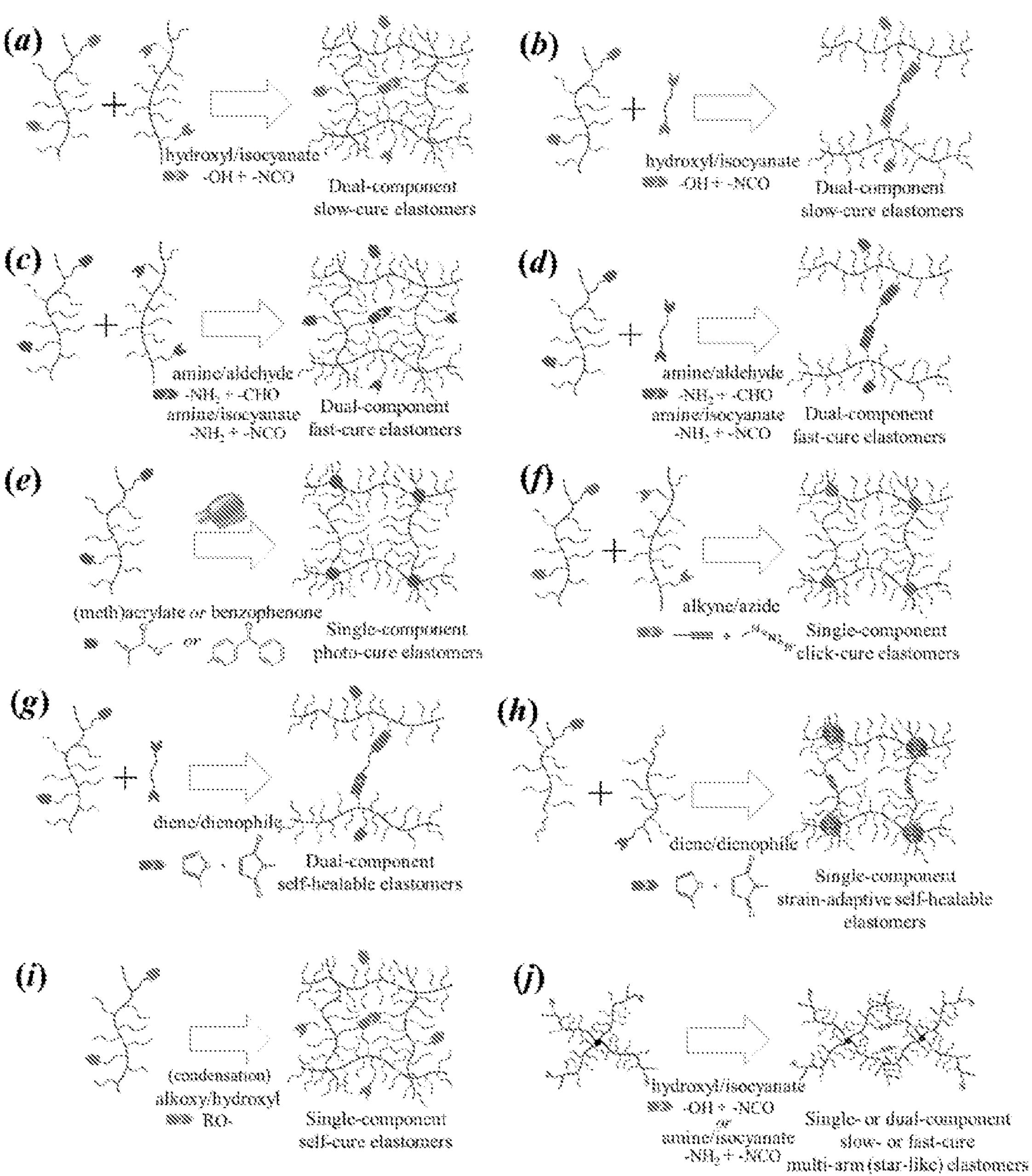
FIGS. 2A-2J show architectures of brush/comb-like tissue-mimetic elastomers with different crosslinking strategies and various features; (2*a*) dual-component slow-cure, (2*b*) single-component slow self-cure, (2*c*), (2*d*) dual-component fast-cure, (2*e*) single-component photo-cure, (2*f*) single-component click-cure, (2*g*) dual-component self-healable, (2*h*) single-component strain-adaptive self-healable elastomers, (2*i*) single-component self-cure, (2*j*) and single- or dual-component slow- or fast-cure multi-arm (star-like) elastomers. It should be noticed that two or more crosslinking strategies may be employed simultaneously to design the disclosed injectable and moldable tissue-mimetic elastomers.
Figure 5A:
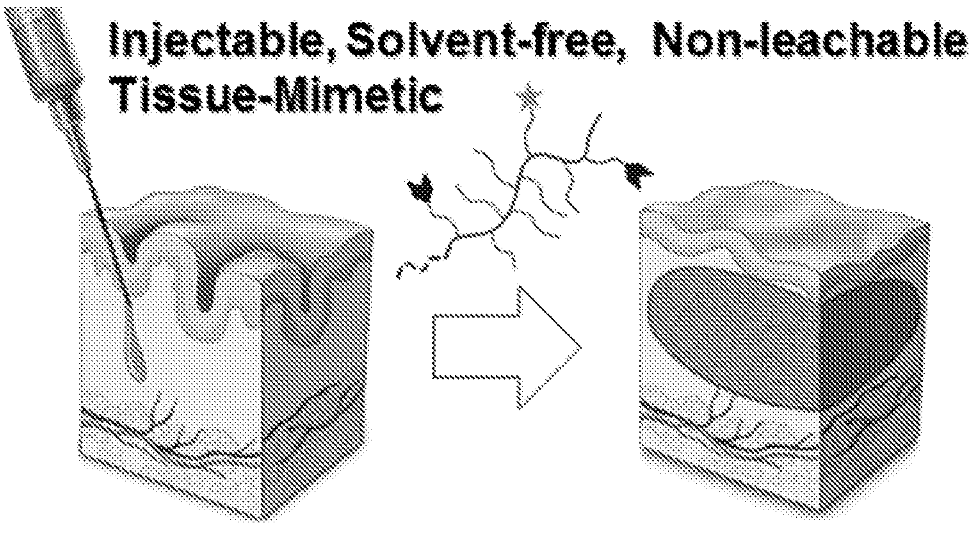
FIG. 5A shows the administration and formation of an implant composed of single- or dual-component injectable tissue-mimetic elastomer, as disclosed herein.

Aldehyde/Amine. In order to synthesize functional bottlebrushes comprising aldehyde groups, above synthesized brush-like chains comprising hydroxyl end groups were treated using UV illumination at predetermined light intensity and exposure time. An alternative route to synthesize functional bottlebrushes comprising aldehyde groups can be through reaction of aforementioned PDMS-r-PEG.$NH_2$ with excess amount of a dialdehyde (e.g., glutaraldehyde). Finally, the dual-component fast-cure tissue-mimetic elastomers were prepared using injection and molding of the brush-like chains comprising aldehyde and amine functional groups through a dual-syringe system (FIG. 2C, 2D).

Photocurable injectable and moldable tissue-mimetic elastomers. To substitute hydroxyl end groups with photocurable methacrylate moieties (FIG. 2E), OH-functionalized bottlebrushes were reacted with excess 2-isocyanatoethyl methacrylate (IEM) in the presence of dibutyltin dilaurate (DBTDL) as catalyst in anhydrous dichloromethane (Scheme (a) above). Subsequently, the functionalized bottlebrushes were precipitated two times in anhydrous dimethylformamide to purify residual IEM and DBTDL. Finally, the functional bottlebrushes were dried with dry air flow until a constant mass was reached. The functionalized brush-like chains were subsequently cured in the presence of a photo-initiator and light illumination.

Diene/Dienophile. To substitute hydroxyl end groups with diene moieties, hydroxyl-functionalized bottlebrushes were reacted with excess furfuryl isocyanate in the presence of DBTDL as catalyst in anhydrous dichloromethane (FIG. 2 G). Bifunctional dienophile crosslinker was synthesized through reaction of chlorine terminated polydimethylsiloxane with 1-(2-hydroxyethyl)-1H-pyrrole-2,5-dione (N-(2-hydroxyethyl) maleimide.

Dried ethanol (2.0 g, 44 mmol), &-caprolactone (60 g, 526 mmol), 100 mL anhydrous toluene was added in an oven-dried flask. To the solution was added 3 Å molecular sieves and the mixture was dried for 48 h. The solution was filtered into a 200 mL round bottom flask. Dibutyltin dilaurate (100 mg) in 1 mL of toluene was added via syringe. The reaction mixture was heated to reflux and aliquots were removed periodically and analyzed by H-NMR. Between 6 and 8 h, the reaction became viscous and magnetic stirring became hard. After reaching to the degree of polymerization equal 10, the reaction was cooled to room temperature. The contents were then poured into methanol chilled in an ice bath to precipitate the polymer. The precipitation procedure was repeated two more times and the polymer filtered, washed with methanol, air dried, and then further dried under a vacuum.

The polymer (10 g, 8.8 mmol) dissolve in 100 mL DCM and dried with anhydrous $MgSO_4$ overnight. The polymer solution was filtered and transferred to a 200 mL oven-dried flask. Triethylamine (1 mL) was added to the flask and the temperature of mixture decrease to 5° C. using ice bath and methacryloyl chloride (1.1 g) in 10 mL anhydrous DCM was added dropwise to the mixture. The ice bath was removed and the temperature was increased to room temperature. The reaction was continued overnight. The mixture was filtered and filtrates were washed with water 3×200 mL. The contents were then concentrated and poured into methanol chilled in an ice bath to precipitate the polymer. The precipitation procedure was repeated two more times and the polymer filtered, washed with methanol, air dried, and then further dried under a vacuum.

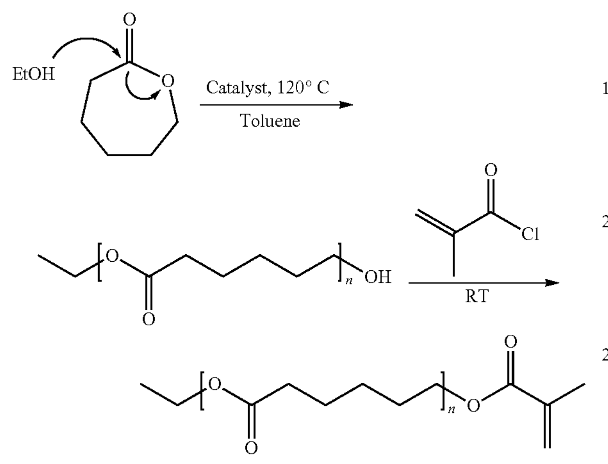

4. Synthesis of Cross-Linker (2)

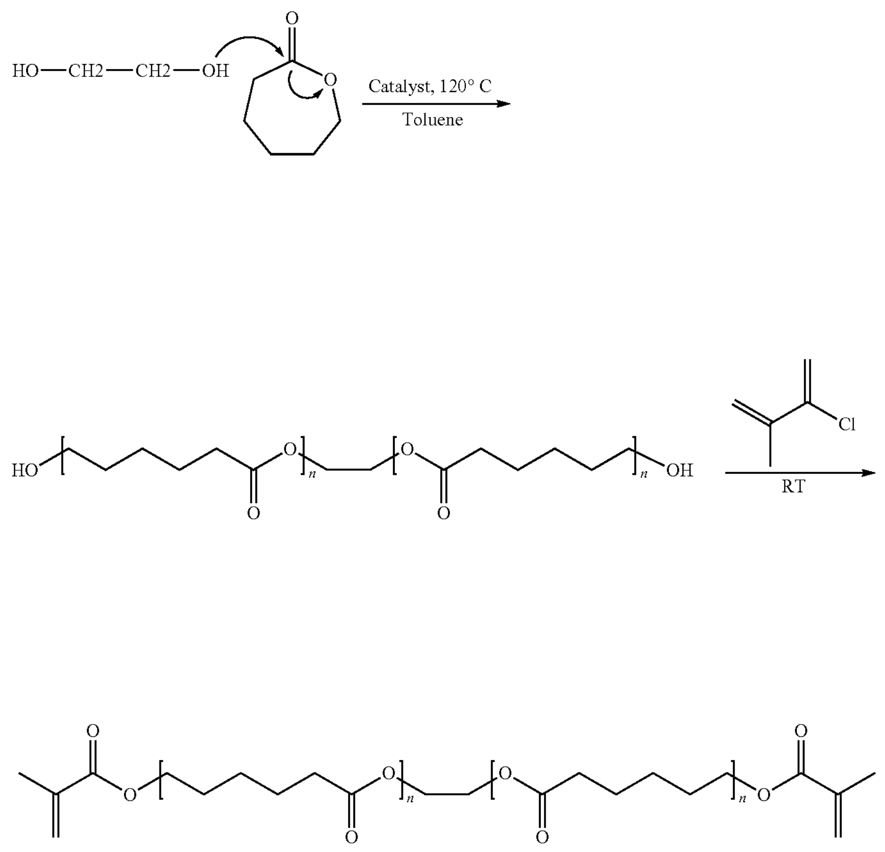

Dried ethylene glycol (1.0 g, 16 mmol), &-caprolactone (46 g, 404 mmol), and 50 mL anhydrous toluene were added to an oven-dried flask. To the solution was added 3 Å molecular sieves and the mixture was dried for 48 h. The solution was filtered into a 200 mL round bottom flask. Dibutyltin dilaurate (100 mg) in 1 mL of toluene was added via syringe. The reaction mixture was heated to reflux and aliquots were removed periodically and analyzed by $^1$H NMR. Between 6 and 8 h, the reaction became viscous and magnetic stirring became hard. After reaching to the degree of polymerization equal 25, the reaction was cooled to room temperature. The contents were then poured into methanol chilled in an ice bath to precipitate the polymer. The precipitation procedure was repeated two more times and the polymer was filtered, washed with methanol, air dried, and then further dried under a vacuum.

The polymer (10 g, 8.8 mmol) was dissolved in 100 mL DCM and dried with anhydrous $MgSO_4$ overnight. The polymer solution was filtered and transferred to a 200 mL oven-dried flask. Triethylamine (1 mL) was added to the flask and the temperature of mixture was decreased to 5° C. using an ice bath before methacryloyl chloride (1.0 g) in 10 mL anhydrous DCM was added dropwise to the mixture. The ice bath was removed and the temperature increased to room temperature. The reaction was continued for overnight. The mixture was filtered and filtrates were washed with water 3×200 mL. The contents were then concentrated and poured into methanol chilled in an ice bath to precipitate the polymer. The precipitation procedure was repeated two more times and the polymer filtered, washed with methanol, air dried, and then further dried under a vacuum.

5. Synthesis of Polycaprolactone Bottlebrushes (DP=800)

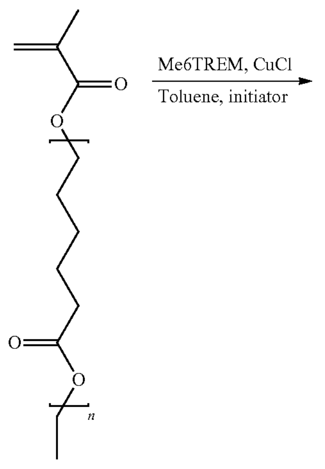

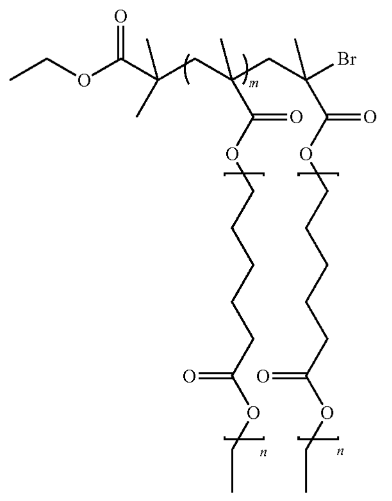

A 25 mL Schlenk flask equipped with a stir bar was charged with EBiB (1.9 mg, 10.0 μmol), pCL monomer (11.4 g, 10.0 mmol), MesTREN (10 μmol), and toluene (10.0 mL). The solution was bubbled with dry nitrogen for 1 hr, then CuCl (0.99 mg, 0.010 mmol) was quickly added to the reaction mixture under nitrogen atmosphere. The flask was sealed, back-filled with nitrogen, purged for 5 minutes, and then immersed in an oil bath thermostated at 45° C. The polymerization was stopped after 10 hrs at 80% monomer conversion, resulting in a bottlebrush pCL polymer with degree of polymerization (DP) of the backbone ($n_{bb}$)~800. The polymer was precipitated three times from methanol to purify, and dried under vacuum at room temperature until a constant mass was reached.

6. pHEMA Synthesis

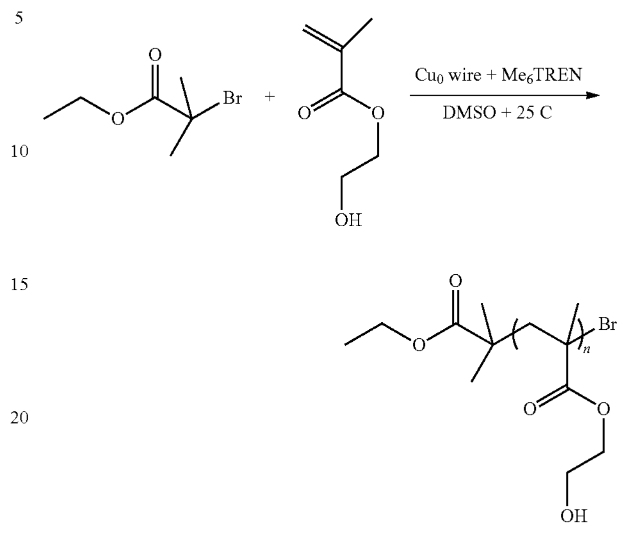

In a 25 mL air free flask, the reagents were added in the following orders under gentle stirring: ethyl bromoisobutyrate (1.95 mg, 0.01 mmol), monomer (HEMA, 1.95 mL, 12 mmol), ligand (Me6-TREN, 0.23 mg, 0.001 mmol) and solvent (DMSO, 4 mL). When the polymerization was performed at this high degree of polymerization a stock solution of ethyl bromoisobutyrate and Me6-TREN in DMSO was prepared. To reduce the viscosity of the polymer with high molecular weight, a DMSO/HEMA volume ratio of 2 was used. The mixture was deoxygenated using seven freeze-pump-thaw cycles from a dry ice/acetone bath. After the last deoxygenation cycle, Cu (0) wire wrapped around a stirring bar was loaded into the reaction vessel under positive argon pressure, at t=0. The reaction vessel as placed in a water bath thermostatted at 25° C. with stirring. The side arm of the flask was purged with argon before it was opened for sampling at the predetermined times with an airtight syringe. At each time, a small amount of the sample was dissolved in $d^6$-DMSO for the analysis of monomer conversion by $^1$H-NMR, to measure the degree of polymerization. The polymerization was stopped by dilution of product with THF when the conversion was reached to 80% and the polymer purified by precipitation of polymer in ether and the rest was kept in a small vial for acetylation.

7. Grafting Through of Caprolactone from Hydroxyl Groups of pHEMA

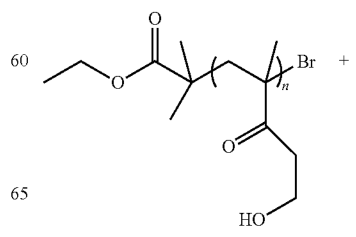

-continued

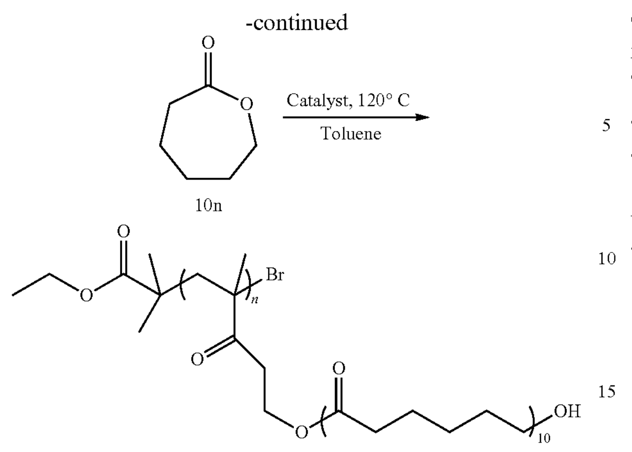

pHEMA (1.5 g, 14 μmol, 11.2 mmol hydroxyl groups) was dissolved in anhydrous DMF (50 mL) in a 100 mL oven dried flask. After complete dissolution, 15.0 g caprolactone and 0.1 g dibutyltin dilaurate were added to the flask and purged with nitrogen for 10 min and was placed in a 110° C. oil bath. The degree of polymerization was tracked by $^1$H-NMR. When the degree of polymerization of caprolactone reached 10, the temperature of the reaction was decreased to room temperature and the polymer was precipitated in ether two times. $^1$H NMR ($CDCl_3$): δ 1.04 0.88 (3H, —$CH_2CH_3$ (COO—)—); 3.65 (2H, —$CH_2CH_3$ (COO—)—), 2.31 (2H, —$COOCH_2$—, PCL) 4.0 (2H, —$CH_2OOC$—, PCL); MW=$8.7\times10^5$ from NMR; PDI=1.36 from GPC.

8. Furan Functionalization of Hydroxyl End Group

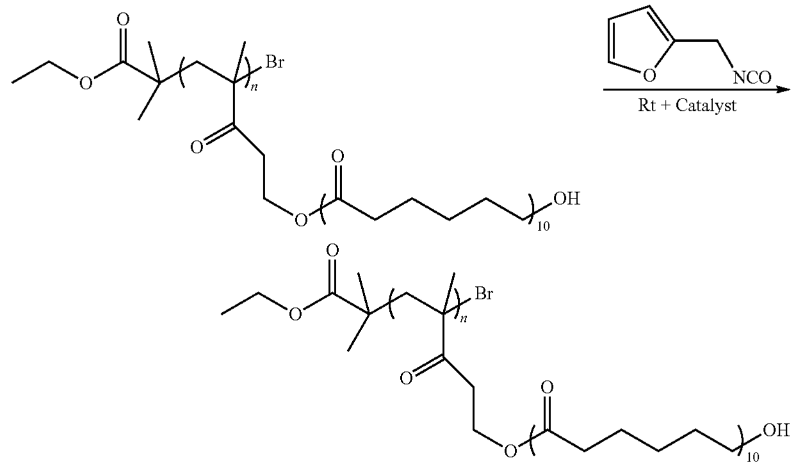

The polymer (pHEMA$_{800}$-g-pCL$_{10}$) (20 g, 21 μmol, 950,000 g/mol) was dissolved in 150 mL anhydrous DCM and oven-dried with anhydrous $MgSO_4$ overnight. The polymer solution was filtered and transferred to a 250 mL oven-dried flask. Dioctyltin dilaurate (100 mg) in 1 mL of anhydrous DCM was added via syringe. Then 0.15 g furan isocyanate was added drop-wise to the flask. The reaction mixture was stirred overnight and analyzed by $^1$H-NMR to measure the average mole percentage of furan groups on the polymer chains. The contents were then concentrated and poured into methanol chilled in an ice bath to precipitate the polymer. The precipitation procedure was repeated two more times and the polymer filtered, washed with methanol, air dried, and then further dried under a vacuum. $^1$H NMR ($CDCl_3$): δ 1.04 0.88 (3H, —$CH_2CH_3$ (COO—)—); 3.65 (2H, —$CH_2CH_3$ (COO—)—), 2.31 (2H, —$COOCH_2$—, PCL) 4.0 (2H, —$CH_2OOC$—, PCL); 6.33 (H, —CHO, furan) 6.23 (H, CH═CHO, furan); 12% furan graft density from NMR.

9. Synthesis of Dimaleimide Cross-Linker (B)

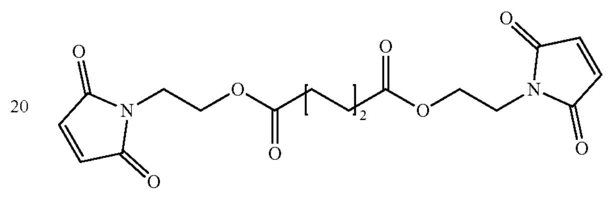

N-(2-Hydroxyethyl) maleimide (4.25 g, 0.03 mol) and 50 mL DCM were added to a 100 mL oven-dried flask. The temperature of the mixture was decreased via an ice bath and 10 mL triethylamine was added to the flask gently with stirring. After complete dissolution, 11.5 g adipoyl chloride was added drop-wise to the reaction over 30 minutes. The reaction temperature was increased to room temperature and the reaction was continued overnight. The mixture was filtered and the filtrate was washed with water 3×200 mL. The mixture was dried using anhydrous $MgSO_4$ overnight and then was filtered and the solvent evaporated to afford a white, solid, powder-shaped product.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and and spirit of the invention being indicated by the following claims.

What is claimed is:

1. A method comprising the steps of:

(a) administering a first liquid polymer formulation to a subject via:

(i) injection into a soft tissue of the subject;

(ii) application onto a surface of a soft tissue of the subject; or (iii) injection into a pre-fabricated soft tissue implant lumen in the subject, wherein the first liquid polymer formulation comprises a plurality of bottlebrush polymers, wherein each bottlebrush polymer has a controlled fraction of end-functionalized side chains, and (b) crosslinking the plurality of bottlebrush polymers via the end-functionalized side chains, thereby forming an elastomer inside the soft tissue of the subject, onto the surface of the soft tissue of the subject, or inside the pre-fabricated soft tissue implant lumen in the subject, wherein the method is solvent-free or substantially solvent-free.

2. The method of claim 1, wherein the method further comprises the step of administering a second liquid polymer formulation to the subject via:

(a) injection into the soft tissue of the subject;

(b) application onto the surface of the soft tissue of the subject; or (c) injection into the pre-fabricated soft tissue implant lumen in the subject, wherein the second liquid polymer formulation comprises a plurality of bottlebrush polymers, wherein each bottlebrush polymer in the second plurality of bottlebrush polymers has a controlled fraction of end-functionalized side chains and wherein step b) comprises crosslinking the plurality of bottlebrush polymers in the first liquid polymer formulation with the plurality of bottlebrush polymers in the second liquid polymer formulation via the end-functionalized side chains on the plurality of bottlebrush polymers in the first liquid polymer formulation and the plurality of bottlebrush polymers in the second liquid polymer formulation.

3. The method of claim 2, wherein the second liquid polymer formulation comprises a polysiloxane, a polyolefin, a polyacrylate, a vinyl polymer, a polyoxazoline, a polyacrylamide, a polyester, a polyglycolide, a polylactide, a poly(lactide-co-glycolide), a polycaprolactone, a poly(ortho ester), a polydioxanone, a polyanhydride, a polyamide, a poly(ester amide), a polymethacrylate, a polyurethane, a polyurea, a poly(propylene fumarate), a poly(glycerol sebacate), a poly(ethylene terephthalate), a polycarbonate, a polystyrene, or a poly(tetrafluoroethylene), or a combination, or copolymer thereof.

4. The method of claim 2, wherein step b) comprises crosslinking a first cross-link moiety on a bottlebrush polymer of the plurality of bottlebrush polymers in the first liquid polymer formulation with a second cross-link moiety on a bottlebrush polymer of the plurality of bottlebrush polymers in the second liquid polymer formulation, wherein the first and second cross-link moieties are different.

5. The method of claim 1, wherein the first liquid polymer formulation comprises a polysiloxane, a polyolefin, a polyacrylate, a vinyl polymer, a polyoxazoline, a polyacrylamide, a polyester, a polyglycolide, a polylactide, a poly (lactide-co-glycolide), a polycaprolactone, a poly(ortho ester), a polydioxanone, a polyanhydride, a polyamide, a poly(ester amide), a polymethacrylate, a polyurethane, a polyurea, a poly(propylene fumarate), a poly(glycerol sebacate), a poly(ethylene terephthalate), a polycarbonate, a polystyrene, or a poly(tetrafluoroethylene), or a combination, or copolymer thereof.

6. The method of claim 1, wherein the first liquid polymer formulation comprises:

(a) a polysiloxane; or (b) a polyolefin comprising polyisobutylene, polyisoprene, polybutadiene, or a combination, or copolymer thereof.

7. The method of claim 1, wherein step b) comprises crosslinking a first cross-link moiety on a bottlebrush polymer of the plurality of bottlebrush polymers in the first liquid polymer formulation with a second cross-link moiety on a second bottlebrush polymer of the plurality of bottlebrush polymers in the first liquid polymer formulation, wherein the first and second cross-link moieties are different.

8. The method of claim 1, wherein the elastomer has an elastic modulus of from about $10^2$ Pa to about $10^9$ Pa.

9. The method of claim 1, wherein the crosslinking is reversible.

10. The method of claim 1, wherein the elastomer is an implant, tissue adhesive, tissue repair, tissue fixation, tissue sealant, wound dressing, liquid bandage, tissue replacement, dermal filler, coating, tissue augmentation, tissue correction, body countering, postsurgical adhesion prevention, or drug delivery system.

11. The method of claim 1, wherein the method comprises administering the first liquid polymer formulation to the subject via injection into the soft tissue of the subject.

12. The method of claim 1, wherein the method comprises administering the first liquid polymer formulation to the subject via injection into the pre-fabricated soft tissue implant lumen in the subject.

13. The method of claim 1, wherein the method comprises administering the first liquid polymer formulation to the subject via application onto the surface of the soft tissue of the subject.

14. The method of claim 1, wherein the first liquid polymer formulation further comprises a plurality of crosslinkers and wherein step b) comprises crosslinking the plurality of bottlebrush polymers with the plurality of crosslinkers via the end-functionalized side chains on the plurality of bottlebrush polymers.

15. The method of claim 1, wherein the method further comprises the step of administering a second liquid polymer formulation to the subject via:

(a) injection into the soft tissue of the subject;

(b) application onto the surface of the soft tissue of the subject; or (c) injection into the pre-fabricated soft tissue implant lumen in the subject, wherein the second liquid polymer formulation comprises a plurality of crosslinkers and wherein step b) comprises crosslinking the plurality of bottlebrush polymers in the first liquid polymer formulation with the plurality of crosslinkers in the second liquid polymer formulation via the end-functionalized side chains on the plurality of bottlebrush polymers in the first liquid polymer formulation.

16. The method of claim 15, wherein the elastomer has a gel fraction up to 98%.

17. The method of claim 1, wherein the method is solvent free.

18. The method of claim 1, wherein the elastomer is substantially non-leaching.

19. The method of claim 1, wherein the cross-linking is without stimuli.

* * * * *